(12) United States Patent
Godwin et al.

(10) Patent No.: US 7,642,403 B2
(45) Date of Patent: Jan. 5, 2010

(54) MARKER MAPPING AND RESISTANCE GENE ASSOCIATIONS IN SOYBEAN

(75) Inventors: Michael Godwin, Virginia Beach, VA (US); Feng Han, Johnston, IA (US); Alec A. Hayes, Chesterfield, VA (US); Xu Hu, Johnston, IA (US); Soon-Chun Jeong, Yuseong-gu (KR); Guihua Lu, Johnston, IA (US); M. A. Saghai Maroof, Blacksburg, VA (US)

(73) Assignees: Pioneer Hi-Bred International, Inc., Johnston, IA (US); Virginia Tech Intellectual Properties, Inc., Blacksburg, VA (US)

(*) Notice: Subject to any disclaimer, the term of this patent is extended or adjusted under 35 U.S.C. 154(b) by 299 days.

(21) Appl. No.: 11/208,038

(22) Filed: Aug. 19, 2005

(65) Prior Publication Data

US 2006/0041955 A1 Feb. 23, 2006

Related U.S. Application Data

(60) Provisional application No. 60/603,983, filed on Aug. 23, 2004.

(51) Int. Cl.
*A01H 1/00* (2006.01)
*A01H 1/02* (2006.01)
*C12N 5/04* (2006.01)
*C12Q 1/68* (2006.01)
*A01H 5/00* (2006.01)

(52) U.S. Cl. .................. 800/267; 800/312; 800/279; 800/265; 800/266; 800/260; 435/6

(58) Field of Classification Search .................. None
See application file for complete search history.

(56) References Cited

U.S. PATENT DOCUMENTS

| 5,689,035 | A | 11/1997 | Webb |
| 5,948,953 | A | 9/1999 | Webb |
| 6,162,967 | A | 12/2000 | Webb |
| 6,355,462 | B1 | 3/2002 | Falco et al. |
| 2006/0015964 | A1 | 1/2006 | Hill et al. |

OTHER PUBLICATIONS

Concibido et al. Crop Science (1997) 37:258-264.*
Polzin et al. J. Hered (1994) 85:300-303.*
Gore et al. Genome (2002):45 (3), pp. 592-599.*
Arahira et al. (2000) "Purification, molecular cloning and ethylene-inducible expression of a soluble0type epoxide hydrolase from soybean (Glycine max [L.] Merr.)." *European Journal of Biochemistry*, 267: 2649-2657.
Bachman et al. (2001) "Molecular Markers Linked to Brown Stem Rot Resistance Genes, $Rps_1$, and $Rbs_2$, in Soybean." *Crop Science*, 41: 527-535.
Cregan et al. (1999) "An Integrated Genetic Linkage Map of the Soybean Genome." *Crop Science*, 39:1464-1490.
GenBank Accession No. AB006748.
GenBank Accession No. AB007126.
GenBank Accession No. AB007127.
GenBank Accession No. AF402603.
GenBank Accession No. BAA77675.
GenBank Accession No. BAA77676.
GenBank Accession No. BAA77677.
Gijzen et al.(2001) "A class I chitinase from soybean seed coat." *Journal of Experimental Botany*, 52(365): 2283-2289.
Graham et at al. (2002) "PCR Sampling of disease resistance-like sequences from a disease resistance gene cluster in soybean." *Theoretical and Applied Genetics*, 105: 50-57.
Hayes et al. (2000) "Molecular Marker Mapping of RSV4, a Gene Conferring Resistance to all Known Strains of Soybean Mosaic Virus." *Crop Science*, 40:1434-1437.
Hayes et al. (2000) "Expression of two soybean resistance gene candidates shows divergence of paralogous single-copy genes." *Theoretical and Applied Genetics*, 101: 789-795.
Ma et al. (1995) "Genetic characteristics of two genes for resistance to soybean mosaic virus in PI486355 soybean." *Theoretical and Applied Genetics*, 91:907-914.
Maughan et al. (2000) "Identification of quantitative trait loci controlling sucrose content in soybean (Glycine max)." *Molecular Breeding*, 6: 105-111.
Song et al. (2004) "A new integrated genetic linkage map of the soybean." *Theoretical and Applied Genetics*, 109:122-128.
Watanabe et al. (1999) "Molecular Cloning and Ethylene0Inducible Expression of Chib1 Chitinase from Soybean (Glycine max (L.) Merr)." *Bioscience, Biotechnology, and Biochemistry*, 63(2): 251-256.
Yang et al. (2001) "Molecular mapping of a new gene for resistance to frogeye leaf spot of soya bean in 'Peking.'" *Plant Breading*, 120: 73-78.
Yeboah et al. (1998) "A Class III acidic endochitinase is specifically expressed in the developing seeds o spybean (Glycine max [L.{ Merr.)." *Plant Molecular Biology*, 36: 407-415.

* cited by examiner

*Primary Examiner*—Medina A Ibrahim
(74) *Attorney, Agent, or Firm*—McKee, Voorhees & Sease, P.L.C.

(57) ABSTRACT

The invention provides novel molecular genetic markers in soybean, where the markers are useful, for example, in the marker-assisted selection of gene alleles that impart disease-resistance, thereby allowing the identification and selection of a disease-resistant plant. The markers also find use in positional cloning of disease-resistance genes.

14 Claims, 6 Drawing Sheets

Fig. 1A

| Fig. 1A |
|---|
| Fig. 1B |
| Fig. 1C |
| Fig. 1D |

| Recombinant Inbred Line | Linkage Group D1b Markers | | | | | | | | | | | Linkage Group J Markers | | | | | | |
|---|---|---|---|---|---|---|---|---|---|---|---|---|---|---|---|---|---|---|
| | SSLP 090 | Satt 216 | Satt 157 | Satt 558 | Satt 542 | Satt 266 | Satt 290 | Satt 41 | Sat 069 | SSLP 048 | SSLP 108 | SSLP 039 | Satt 529 | Sct 001 | Satt 244 | Satt 431 | RGA 43 | SSLP 181 |
| VRI-1 | A | A | A | A | A | B | A | A | A | A | B | - | - | - | A | - | - | A |
| VRI-2 | B | B | - | B | B | A | A | A | A | B | B | B | A | B | B | A | A | B |
| VRI-3 | A | A | A | A | A | A | A | A | A | A | A | - | - | A | A | A | A | A |
| VRI-4 | B | B | B | B | A | B | B | B | A | B | - | A | B | B | A | A | A | A |
| VRI-5 | B | B | B | B | B | B | B | B | A | B | B | B | A | B | A | A | A | B |
| VRI-6 | A | A | A | A | B | A | A | A | B | A | B | B | A | A | B | B | A | A |
| VRI-7 | B | - | B | B | B | B | B | B | A | - | B | A | B | B | B | A | B | B |
| VRI-8 | B | - | - | B | B | B | B | B | A | B | A | B | A | A | A | A | B | A |
| VRI-9 | B | B | - | - | A | A | B | A | A | - | - | A | A | B | - | A | A | - |
| VRI-10 | B | B | B | B | B | A | A | A | B | B | B | B | B | B | A | B | B | B |
| VRI-11 | B | B | B | A | B | A | A | B | A | B | A | A | A | A | A | A | - | - |
| VRI-12 | A | B | A | A | B | B | A | A | B | A | A | A | A | A | A | - | A | - |
| VRI-13 | A | A | B | B | B | A | B | A | - | A | A | B | A | B | B | - | - | - |
| VRI-14 | B | A | A | A | B | A | A | B | B | B | - | - | B | B | A | B | A | A |
| VRI-15 | A | B | A | A | A | B | B | A | A | B | B | A | B | B | B | B | B | - |
| VRI-16 | B | B | B | B | B | B | A | B | B | A | A | - | B | B | A | - | A | B |
| VRI-17 | B | A | B | B | B | A | B | A | B | B | A | A | B | B | A | - | - | B |
| VRI-18 | A | A | B | B | A | A | A | A | A | - | A | B | B | B | B | A | B | - |
| VRI-19 | A | A | A | B | B | A | B | A | A | A | B | A | B | B | B | B | A | - |
| VRI-20 | B | A | B | B | B | A | A | A | - | A | B | B | B | B | B | B | B | - |

Fig. 1B

| Recombinant Inbred Line | Linkage Group D1b Markers | | | | | | | | | | | | Linkage Group J Markers | | | | | | | |
|---|---|---|---|---|---|---|---|---|---|---|---|---|---|---|---|---|---|---|---|---|
| | SSLP 090 | Satt 216 | Satt 157 | Satt 558 | Satt 542 | Satt 266 | Satt 290 | Satt 41 | Sat 069 | SSLP 048 | SSLP 108 | SSLP 039 | Satt 529 | Sct 001 | Satt 244 | Satt 431 | RGA 43 | SSLP 181 |
| VRI-22 | A | A | - | - | A | - | A | - | - | A | A | - | - | - | - | A | - | - |
| VRI-23 | A | B | - | A | A | A | A | A | A | B | A | B | A | A | - | B | - | A |
| VRI-24 | A | A | A | A | B | A | A | A | A | A | - | - | - | A | B | - | - | A |
| VRI-25 | B | A | B | B | B | B | B | B | B | A | - | B | B | B | B | - | B | B |
| VRI-26 | A | A | A | A | A | A | A | A | A | A | A | A | A | A | A | A | A | - |
| VRI-27 | B | B | A | B | B | A | B | A | A | B | - | B | A | A | B | - | B | A |
| VRI-28 | B | A | B | B | B | B | B | A | B | A | B | B | B | B | B | B | B | - |
| VRI-29 | B | A | A | B | B | B | B | B | A | - | B | B | A | A | A | - | - | A |
| VRI-30 | B | A | - | - | B | - | - | A | A | A | B | B | A | B | - | B | B | - |
| VRI-31 | B | B | B | B | B | B | A | B | B | B | - | B | B | A | B | B | B | B |
| VRI-32 | A | A | A | A | A | B | - | A | A | A | - | A | A | - | A | A | A | - |
| VRI-34 | B | A | B | B | B | B | B | A | A | B | A | B | A | A | A | A | A | A |
| VRI-35 | A | A | A | A | A | A | B | A | A | B | - | B | B | A | A | B | A | A |
| VRI-36 | B | B | B | B | B | A | A | B | A | A | A | A | - | A | B | A | B | B |
| VRI-37 | B | - | A | - | - | - | B | - | - | - | B | B | - | B | A | A | A | B |
| VRI-38 | A | A | A | B | A | B | A | A | A | B | A | A | A | A | A | A | - | A |
| VRI-39 | B | B | B | B | B | B | A | B | B | B | B | B | B | B | B | B | B | - |
| VRI-40 | B | A | A | A | A | B | A | A | A | A | A | A | A | A | A | A | A | B |
| VRI-41 | A | B | A | B | B | B | B | A | B | B | A | B | A | A | A | A | A | A |
| VRI-42 | B | A | B | A | A | A | A | A | A | B | - | A | - | A | A | B | B | - |
| VRI-43 | A | A | A | B | B | A | B | B | B | A | A | B | A | A | B | A | A | B |
| VRI-44 | A | B | B | B | B | B | A | A | A | B | B | A | B | B | A | B | B | A |
| VRI-45 | B | A | A | B | B | B | A | A | A | A | A | B | A | A | A | A | B | - |
| VRI-46 | B | A | B | B | B | B | B | A | B | B | B | B | A | B | B | B | B | B |
| VRI-47 | B | B | B | B | B | B | B | B | B | B | A | A | B | A | A | A | A | B |
| VRI-48 | B | B | A | A | A | A | A | A | A | A | A | A | B | A | A | B | B | A |
| VRI-49 | B | B | A | B | A | A | B | B | A | B | B | B | A | B | A | A | - | - |
| VRI-50 | B | B | A | A | A | A | A | A | A | A | A | A | A | B | B | A | B | B |
| VRI-51 | B | - | A | B | - | - | B | A | A | B | - | A | B | A | A | A | A | B |
| VRI-52 | B | A | B | B | B | - | B | B | A | B | B | B | B | B | B | B | B | B |
| VRI-53 | B | B | B | B | B | B | B | B | B | B | B | B | B | B | B | B | B | A |

Fig. 1C

| Recombinant Inbred Line | Linkage Group D1b Markers | | | | | | | | | | | SSLP 039 | Linkage Group J Markers | | | | | |
|---|---|---|---|---|---|---|---|---|---|---|---|---|---|---|---|---|---|---|
| | SSLP 090 | Satt 216 | Satt 157 | Satt 558 | Satt 542 | Satt 266 | Satt 290 | Satt 41 | Sat 069 | SSLP 048 | SSLP 108 | | Satt 529 | Sct 001 | Satt 244 | Satt 431 | RGA 43 | SSLP 181 |
| VRI-54 | A | B | A | A | B | B | B | B | B | B | B | B | - | A | B | - | B | A |
| VRI-56 | B | A | B | B | B | B | - | - | - | A | B | A | A | A | A | - | A | - |
| VRI-57 | B | B | B | B | B | B | - | B | B | B | B | B | A | A | B | - | - | A |
| VRI-58 | B | A | - | B | B | A | A | A | A | A | B | A | B | B | A | - | A | B |
| VRI-59 | A | A | A | A | - | B | - | B | A | B | - | A | A | A | B | - | B | A |
| VRI-60 | B | B | B | B | - | A | B | A | B | B | A | B | B | B | A | - | B | - |
| VRI-61 | - | - | - | - | - | - | - | - | - | - | - | - | - | - | - | - | - | - |
| VRI-62 | B | B | B | B | - | A | A | A | B | B | B | B | B | B | A | B | B | A |
| VRI-63 | B | A | B | B | - | - | A | A | A | A | A | A | A | B | B | A | A | B |
| VRI-64 | B | B | B | B | A | B | A | A | B | B | - | A | A | B | B | B | B | A |
| VRI-66 | B | A | B | B | - | A | B | B | A | B | - | B | A | B | A | A | B | B |
| VRI-67 | A | A | A | A | A | A | A | A | A | A | B | A | A | A | A | B | A | A |
| VRI-68 | A | A | A | A | - | B | A | A | B | A | B | B | - | A | B | A | A | A |
| VRI-69 | A | - | B | A | - | B | - | A | A | - | A | - | A | - | - | B | - | - |
| VRI-70 | B | - | - | B | - | - | A | B | - | B | - | B | - | A | B | - | - | - |
| VRI-71 | - | - | - | - | - | - | - | - | - | - | - | - | - | - | - | - | - | - |
| VRI-72 | B | - | - | - | A | A | A | A | A | - | - | - | - | A | A | - | - | A |
| VRI-73 | A | A | A | A | A | B | B | B | B | B | B | A | A | A | A | A | A | A |
| VRI-74 | A | - | B | A | A | A | A | A | A | A | - | A | B | B | B | B | B | B |
| VRI-75 | A | A | B | B | - | B | B | B | B | B | B | A | B | B | B | B | B | B |
| VRI-76 | A | A | A | B | B | - | A | A | A | A | - | B | B | B | B | B | B | B |
| VRI-77 | B | B | B | B | B | B | B | A | B | B | B | A | A | B | A | A | A | A |
| VRI-78 | B | B | B | A | A | A | A | B | A | A | A | A | B | B | B | B | B | B |
| VRI-79 | A | A | B | B | B | - | B | A | A | B | - | A | A | A | A | A | A | A |
| VRI-80 | - | A | - | A | A | A | A | A | - | A | B | A | A | A | A | A | A | A |
| VRI-81 | - | - | A | - | - | - | B | B | A | - | A | A | A | A | A | A | A | A |
| VRI-82 | A | B | A | A | B | A | A | A | A | B | - | A | B | A | A | A | A | B |
| VRI-83 | - | B | A | - | B | - | B | B | A | A | B | B | B | B | B | B | B | A |
| VRI-84 | A | - | B | B | A | A | A | A | A | A | A | A | A | A | A | A | A | A |
| VRI-85 | - | A | A | - | B | - | A | A | B | B | B | A | B | B | B | B | B | B |
| VRI-86 | A | A | A | A | A | A | A | A | A | A | A | A | A | A | A | A | A | A |
| VRI-87 | - | - | - | - | - | - | - | - | - | - | - | - | - | - | - | - | - | - |

Fig. 1D

| Recombinant Inbred Line | Linkage Group D1b Markers | | | | | | | | | | | Linkage Group J Markers | | | | | | |
|---|---|---|---|---|---|---|---|---|---|---|---|---|---|---|---|---|---|---|
| | SSLP 090 | Satt 216 | Satt 157 | Satt 558 | Satt 542 | Satt 266 | Satt 290 | Satt 41 | Sat 069 | SSLP 048 | SSLP 108 | SSLP 039 | Satt 529 | Sct 001 | Satt 244 | Satt 431 | RGA 43 | SSLP 181 |
| VRI-88 | A | B | A | A | - | A | A | A | B | B | - | B | A | A | B | B | B | A |
| VRI-89 | B | B | B | B | B | B | B | B | A | - | B | - | B | B | A | A | A | A |
| VRI-90 | B | - | B | B | B | B | B | B | B | - | B | A | A | A | A | A | A | A |
| VRI-91 | B | B | B | B | B | B | B | B | B | B | B | B | B | B | B | B | A | B |
| VRI-92 | B | A | B | B | B | - | - | A | A | A | - | B | B | B | B | A | A | B |
| VRI-93 | A | A | A | A | A | B | A | B | A | A | A | A | B | B | A | B | - | A |
| VRI-94 | B | B | B | B | B | B | B | B | B | B | B | A | A | A | A | A | B | A |
| VRI-95 | B | - | A | A | A | B | - | A | A | B | B | B | B | B | A | A | A | A |
| VRI-96 | A | B | B | B | B | A | B | B | B | B | A | A | A | A | A | A | A | B |
| VRI-97 | B | B | B | B | B | B | B | B | A | B | A | B | B | B | B | B | B | B |
| VRI-98 | B | A | B | B | A | A | A | A | B | - | B | B | A | A | A | A | A | - |
| VRI-99 | A | A | A | A | A | B | B | B | A | A | A | A | B | B | B | A | - | - |
| VRI-100 | A | A | B | A | B | - | - | B | B | A | - | A | A | A | A | A | A | A |
| VRI-101 | B | A | B | B | A | B | B | B | A | - | - | B | B | B | B | A | A | A |
| VRI-102 | B | B | B | B | - | B | B | B | B | - | - | A | A | A | A | A | B | B |
| VRI-103 | B | B | B | B | - | B | B | B | A | B | - | B | B | B | B | B | A | A |
| VRI-104 | A | B | B | A | B | A | B | A | B | B | A | B | B | B | B | B | - | A |
| VRI-105 | B | B | B | B | B | B | B | B | A | B | - | B | A | A | A | A | B | B |
| VRI-106 | B | B | B | A | A | A | A | A | A | - | - | B | B | B | B | A | A | A |
| VRI-107 | A | B | A | A | A | A | A | B | - | - | - | A | A | A | A | A | B | - |
| VRI-108 | - | - | B | - | - | - | - | - | - | - | - | B | B | B | B | B | B | A |
| VRI-109 | B | B | B | A | A | B | B | B | - | B | - | A | A | A | A | A | A | B |
| VRI-110 | A | B | A | A | A | A | A | A | A | A | - | B | A | A | A | B | B | A |
| VRI-111 | B | B | B | B | A | B | B | B | - | B | - | B | B | B | B | B | B | B |
| VRI-112 | A | A | A | A | - | A | A | - | - | - | - | B | B | B | B | B | B | - |
| VRI-113 | A | A | B | A | A | B | B | B | B | - | - | B | A | A | B | B | B | A |
| VRI-114 | A | A | B | B | B | B | A | B | B | A | - | B | B | B | B | B | B | B |
| VRI-115 | B | - | A | B | - | - | B | - | - | - | B | B | B | B | B | B | B | B |
| VRI-116 | A | A | A | A | A | B | B | B | B | A | B | - | B | B | B | B | B | - |
| VRI-117 | B | A | B | A | A | B | B | A | B | A | - | A | A | A | A | A | A | A |
| VRI-118 | A | B | A | A | B | B | - | B | B | B | B | A | B | B | A | A | A | B |

1

MARKER MAPPING AND RESISTANCE GENE ASSOCIATIONS IN SOYBEAN

CROSS-REFERENCE TO RELATED APPLICATIONS

This application claims priority to and benefit of U.S. Provisional Patent Application Ser. No. 60/603,983, filed on Aug. 23, 2004, the specification of which is hereby incorporated by reference in its entirety.

FIELD OF THE INVENTION

The invention relates to novel molecular genetic markers in soybean, where the markers are useful, for example, in the marker-assisted selection of gene alleles that impart disease-resistance, thereby allowing the identification and selection of a disease-resistant plant.

BACKGROUND OF THE INVENTION

Soybean, a legume, has experienced increasing importance in the world economy, and has become the world's primary source of seed oil and seed protein. Both people and livestock rely on soybeans as a food source. In addition, its utilization is being expanded to the industrial, manufacturing and pharmaceutical sectors. Soybean productivity, well-being and improvement are vital agricultural considerations.

Soybean is host to one of the widest ranges of infectious pathogens of all crops. Finding resistance to these many pathogens is crucial to preventing devastating yield losses. More than a hundred different pathogens are known to affect soybeans, and all parts of the plant are susceptible to disease. Of these documented pathogens, approximately 35 pose significant economic threats. It is rare to find a soybean field that is pathogen-free, and in most instances, plants are infected with multiple diseases.

Efforts to improve the soybean crop have benefited greatly by the evolution of plant genomics, and more specifically, genetic linkage maps and molecular marker technology. Plant genetic variability that can be detected at the molecular level has been a great benefit for crop improvement research. It has also permitted the direct manipulation of specific genes through cloning and transformation techniques.

Genetic Linkage Maps

A genetic map, also termed a linkage map, is a representation of a genome that shows the relative positions of specific DNA markers relative to each other. The construction of linkage maps is based solely on the ability to identify genetic markers. Any differentially inherited polymorphic trait that segregates among progeny is a potential marker. Linked markers are markers that are relatively close to each other on the genetic map, and as a result, are co-inherited with a characteristic non-random frequency (a frequency greater than 51%). The closer they lie to each other on the genetic map, the lower the likelihood they will independently segregate following crossing-over events, and the greater the likelihood the two markers will be co-inherited. This is the underlying principle used in all linkage determinations and by all computational programs to construct genetic linkage maps. A variety of programs for the analysis of mapping data are available, and include, for example, Mapmaker, MapManager, MultiMap and LINKAGE.

In general, the closer two markers are on the genetic map, the closer they lie to each other on the physical map. A relative genetic distance (determined by crossing over frequencies, measured in centimorgans; cM) is generally proportional to the physical distance (measured in base pairs [bp], e.g., kilobase pairs [kb] or megabase pairs [Mbp]) that two linker marker are separated on a linkage group (a chromosome).

Genetic linkage maps that produce tightly linked markers are beneficial to marker-assisted selection (MAS) breeding programs. In this technique, researchers employ markers (typically molecular markers) to improve the efficiency of selecting gene alleles that impart a beneficial trait, e.g., disease resistance. In any genetic analysis, including MAS, a genetic map that contains a certain number of makers is more useful than a genetic map that contains fewer markers. If a map can be saturated with a sufficient number of linked markers for traits of interest, then gene (trait) mapping and gene cloning, e.g., positional cloning, are facilitated.

Molecular Markers

Plant genetic variability that can be detected at the molecular level has been a great benefit for crop improvement research. These molecular markers can be categorized into two broad classes, namely, restriction fragment length polymorphisms (RFLPs) and microsatellites.

RFLP markers are hybridization-based molecular markers. RFLPs produce different size fragments when cleaved by restriction enzymes because of the variation in the DNA primary structure. These different size fragments are then resolved and detected using various gel-based assays, including Southern blotting using radioactive or non-radioactive labeled probes. RFLP genetic analysis is hindered by technical considerations including probe design, restriction enzyme choice and molecular weight of the segregating bands. Adding to these limitations is the low level of polymorphism detectable by RFLP techniques, requirement for larger amounts of genetic material, and result in poorer genetic resolution than methods that detect other types of heterogeneity (e.g., SSR-type microsatellite heterogeneity). RFLP analysis is labor-intensive and time consuming, and cost of this procedure can become prohibitively expensive when compared to other methods.

The term simple sequence repeat (SSR), or microsatellite, refer generally to short (typically up to several hundred base pairs) segment of DNA that consists of multiple tandem repeats of a two or three base-pair sequence. These repeated sequences result in DNA regions of variable length. These repetitive sequences demonstrate poor replication fidelity due to polymerase slippage, and result in highly polymorphic regions. Microsatellites appear to be randomly dispersed through the genome and are generally flanked by conserved regions. This genomic variability is inherited and reproducibly detectable. These characteristics of SSRs are well suited for amplification as PCR products, leading to their extensive development as molecular markers.

SSLP-type heterogeneity is generally heterogeneity caused by small insertions or deletions that result in changes in the length of the polymorphic region. In some cases, SSRs are a subset of SSLP heterogeneity, and can encompass any molecular event that alters the basepair length at a specific location in the DNA (resulting in polymorphism). The SSLP-type polymorphic region is identified and amplified with primers similar to SSR methods. Thus, the SSLP scheme includes, but is not limited to, SSR-type polymorphism. As used herein, reference to SSLP polymorphisms generally includes SSR-type polymorphisms.

The characteristics of microsatellite heterogeneity make them well suited for use a molecular genetic markers. The use of amplification-based detection techniques such as PCR has led to their extensive development as molecular markers.

Microsatellite markers are generated as PCR amplicons that span polymorphic regions containing repeats or deletions/insertions, where the PCR primers lie in conserved domains that flank the microsatellite repeats. The PCR product corresponds to the length of the microsatellite region, and will produce PCR products with characteristic and reproducible sizes. Useful polymorphic microsatellite regions can include any mutational event that alters the length of the amplified sequence.

The proliferation of increasingly sophisticated amplification-based detection techniques provides a variety of sensitive methods for the detection of genetic variation at the nucleotide level. Primers or probes are designed for high levels of sequence specificity, which allows precise DNA regions of interest to be targeted. These types of molecular markers offer the potential for high throughput, increased efficiency and reduced expense.

The nature of polymorphism in SSRs gives SSR-based markers several distinct advantages over hybridization-based methods such as RFLP analysis. Most significantly, an SSR marker can detect multiple alleles, manifested as different sized PCR amplicons. As long as there exist at least two gene alleles that produce PCR products with two different sizes, the SSRs can be employed as a marker. The ability to visualize both parental bands in progeny also allows heterozygosity to be monitored, which is not possible when scoring is based on the presence or absence of a marker alone (as with most random amplified polymorphic DNA (RAPD) marker analysis).

Expressed Sequence Tags (ESTs) are cDNA clones that correspond to expressed mRNA. These sequences are termed tags because typically only a few hundred nucleotides are sequenced from the cDNA for identification purposes only. Human and mouse genomes have demonstrated the usefulness of ESTs in genetic linkage map construction and map-based cloning; however, their application in plant systems has been limited, due in part to the scarcity of plant EST databases.

Predicting the presence or absence of a particular gene allele (e.g., a disease resistance allele) is one of the most desired qualities in molecular markers. The closer a marker is to a gene allele, the better it serves to tag the desired allele. The ability to include more markers in the soybean genetic map will greatly improve the ability to detect and select for desired traits (e.g., disease resistance). SSR/SSLP markers derived from ESTs offer an opportunity to improve soybean genetic maps. Furthermore, since the sequences that are being mapped are derived from functional sequences, it is possible that an EST marker that maps very close to or on top of a desired phenotypic trait is in fact derived from the gene that encodes that desired trait, thereby permitting and providing a basis for cloning of the genomic locus and expressed allele that imparts that desired trait.

There is a need in the art for improved soybean genetic maps to facilitate the study of disease-resistance genetic loci. There is a need for soybean molecular markers to construct genetic maps with improved resolution, especially in the vicinity of known disease resistance loci. There is a need in the art for soybean molecular markers that are in close proximity to disease-resistance loci in order to facilitate marker assisted selection (MAS), genetic analysis of those genetic loci, and also to facilitate gene discovery and cloning of the gene alleles that impart the disease resistance. The present invention provides compositions and methods that meet these needs and provide other advantages.

SUMMARY OF THE INVENTION

The invention provides a variety of compositions and methods to benefit the soybean plant breeder. These compositions and methods find use in the identification, selection and construction of soybean plants that have resistance or improved resistance to various fungal or viral plant diseases. These compositions and methods of the invention utilize EST-derived molecular genetic markers.

The invention provides methods for detecting disease-resistant plants using EST-derived molecular genetic markers that map close to known disease-resistance loci in the soybean genome. In these methods, a disease-resistant soybean plant is selected by first detecting an EST-derived marker nucleic acid mapping ten centimorgans or less from a disease-resistance gene allele. The disease resistance genes can be, for example, soybean mosaic virus resistance gene 4 (Rsv4), frogeye leaf spot resistance gene (Rcs3), brown stem rot resistance gene 1 (Rbs1), brown stem rot resistance gene 2 (Rbs2) or brown stem rot resistance gene 3 (Rbs3). A disease resistant plant can be selected by selecting a plant having the marker nucleic acid.

In some embodiments, detection of the marker nucleic acid (or a portion of the marker) is made by any suitable method of marker amplification, for example, by using the polymerase chain reaction (PCR) using a nucleic acid from the plant as a template in the PCR. In some embodiments, the PCR reaction uses a primer pair having the nucleotide sequence of SEQ ID NOs: 3 and 4, or the nucleotide sequence of SEQ ID NOs: 5 and 6.

In some embodiments, the EST-derived marker used in the detection (e.g., by PCR amplification) and selection is the nucleotide sequence shown in SEQ ID NO: 1 (SSLP039 full length EST), the nucleotide sequence shown in SEQ ID NO: 2 (SSLP090 full length EST), a portion of at least 20 contiguous nucleotides of SSLP039 or SSLP090, or a nucleotide sequence complementary to any of these sequences.

In other aspects, the soybean plant under study is a progeny plant that resulted from a plant cross between a first soybean plant having the disease-resistance gene allele and a second plant that does not have the disease-resistance gene allele. In some aspects, the disease-resistance gene allele is introgressed into offspring soybean progeny.

The invention also provides disease-resistant soybean plants produced by any of the methods described above. These plants are resistant, for example, to (a) viral infections that cause soybean mosaic disease, (b) fungal infections that cause frogeye leaf spot, or (c) fungal infections that cause brown stem rot.

The invention also provides tools for the plant molecular geneticist to clone nucleic acids that encode disease-resistance genes. In some aspects, the EST-derived soybean markers can be used to positionally clone nearby resistance genes, or alternatively, the EST-derived marker itself is a portion of a gene that imparts disease resistance, and a full length gene (e.g., a full length cDNA) or suitable portion thereof can be isolated using standard methods known in the art.

In some aspects, the invention provides methods for the positional cloning of soybean genomic nucleic acids having within their sequence a disease-resistance gene allele. Using this technique, a soybean genomic nucleic acid carrying the disease-resistance gene allele and an EST-derived marker mapping ten centimorgans or less from the disease-resistance gene allele is identified. Disease resistance alleles can include, for example, alleles of soybean mosaic virus resistance gene 4 (Rsv4), frogeye leaf spot resistance gene (Rcs3), brown stem rot resistance gene 1 (Rbs1), brown stem rot resistance gene 2 (Rbs2) and brown stem rot resistance gene 3 (Rbs3). Having identified and isolated a genomic clone having the EST marker sequence, the disease-resistance gene allele is thereby cloned (e.g., by positional cloning) by taking advantage of its proximity to the EST marker sequence.

Generally, in such cloning methods, the identification of genomic DNA clones containing a disease-resistance gene allele is accomplished by admixing an EST marker-specific probe with a soybean genomic nucleic acid library, where the probe is complementary or partially complementary to at least a portion of the EST marker sequence, and detecting a hybridization complex between the probe and a genomic nucleic acid clone from the library. The probe used in this cloning strategy can have a variety of polynucleotide sequences, for example; (a) a polynucleotide sequence shown in SEQ ID NO: 1 (SSLP039); (b) a polynucleotide sequence shown in SEQ ID NO: 2 (SSLP090); (c) a unique polynucleotide subsequence that is a portion of at least 20 contiguous nucleotides of (a) or (b); and, (d) a polynucleotide sequence having at least 70% sequence identity with the polynucleotide sequence of (a), (b) or (c), other than a sequence encoded by GenBank Accession Number AB006748, AB007126, AB007127 or AF402603.

In some embodiments, the positional cloning methods identify a preferred genomic clone by admixing an amplification primer or amplification primer pair with a soybean genomic nucleic acid library, where the primer or primer pair is complementary or partially complementary to at least a portion of the EST marker nucleic acid, and is capable of initiating DNA polymerization by a DNA polymerase on a soybean genomic nucleic acid template, and extending the primer or primer pair in a DNA polymerization reaction using a DNA polymerase and a template genomic nucleic acid clone from the library to generate at least one amplicon, thereby identifying a genomic nucleic acid comprising the disease-resistance gene allele. The resulting amplicon can include, for example, (i) the nucleotide sequence of SEQ ID NO: 1 (SSLP039); (ii) the nucleotide sequence of SEQ ID NO: 2 (SSLP090); (iii) a portion of at least 20 contiguous nucleotides of (i) or (ii); (iv) a nucleotide sequence that comprises at least 70% sequence identity with the nucleotide sequence of (i), (ii) or (iii), where the nucleotide sequence that is at least 70% identical is other than a sequence encoded by GenBank Accession Number AB006748, AB007126, AB007127 or AF402603; or (v) a complementary nucleic acid of (i), (ii) or (iii).

In some embodiments of the positional cloning method, a contig map is created that encompasses the disease-resistance gene and the EST marker nucleic acid. The contig map comprises one or more overlapping soybean genomic nucleic acids, and the map is constructed prior to the identifying the EST-derived marker on the map.

In some aspects, the invention provides nucleic acids. These nucleic acids have a variety of uses, including, for example, amplification primers or amplification primer pairs that are specific for the EST-derived markers of the invention (e.g., SSLP039 and SSLP090), and are capable of generating a marker-specific amplicon. In some aspects where a single amplification primer is used, the primer is capable of initiating DNA polymerization by a DNA polymerase on a soybean nucleic acid template to generate a single-stranded amplicon, where the amplicon comprises, (i) the nucleotide sequence of SEQ ID NO: 1 (SSLP039), where the amplification primer is complementary or partially complementary to the first 29 nucleotides of SEQ ID NO: 1; (ii) the nucleotide sequence of SEQ ID NO: 2 (SSLP090); (iii) a portion of at least 20 contiguous nucleotides of (i) or (ii); or (iv) a complementary nucleic acid of (i), (ii) or (iii).

Similarly, the invention also provides amplification primer pairs that are capable of initiating DNA polymerization by a DNA polymerase on a soybean nucleic acid template to generate a double-stranded amplicon, where the amplicon comprises, (i) the nucleotide sequence of SEQ ID NO: 1 (SSLP039), where one member of the amplification primer pair is complementary or partially complementary to the first 29 nucleotides of SEQ ID NO: 1; (ii) the nucleotide sequence of SEQ ID NO: 2 (SSLP090); or (iii) a portion of at least 20 contiguous nucleotides of (i) or (ii). More specifically, the amplification primer pairs can be selected from the nucleotide sequences of SEQ ID NOs: 3 and 4, or the nucleotide sequence of SEQ ID NOs: 5 and 6.

The invention also provides a variety of other nucleic acids, for example, nucleic acids that can be used as probes, amplicons that are indicative of the presence of a marker sequence, or nucleic acids that encode polypeptides that impart disease-resistance when expressed in a plant. These various nucleic acids include, for example, (a) a polynucleotide corresponding to SEQ ID NO: 1 (SSLP039) or SEQ ID NO: 2 (SSLP090); (b) a unique subsequence of (a); (c) a polynucleotide that hybridizes under stringent conditions to the nucleic acid of (a) that is a polynucleotide sequence other than a sequence encoded by GenBank Accession Number AB006748, AB007126, AB007127 or AF402603; (d) a polynucleotide encoding a polypeptide comprising at least 138 contiguous amino acids of SEQ ID NO: 7 (SSLP039); (e) a polynucleotide that is at least about 70% identical to a polynucleotide sequence corresponding to SEQ ID NO: 2 (SSLP090); (f) a polynucleotide comprising a portion of at least 258 contiguous nucleotides of SEQ ID NO: 1 (SSLP039); (g) a polynucleotide comprising a portion of at least 23 contiguous nucleotides of SEQ ID NO: 2 (SSLP090); and, (h) a polynucleotide complementary to a polynucleotide of (a)-(g). As one familiar with the art is well aware, nucleic acids, including those of the invention, are nto limited to naturally occurring nucleic acid structures; for example, the nucleic acids of the invention can utilize nucleotides, modified nucleotides, polynucleotide analogs, one or more unnatural bases or any combination thereof.

In some embodiments, the nucleic acid of the invention encodes a polypeptide having chitinase activity. In some aspects, the nucleic acid of the invention is in a vector, for example, an expression vector. In some aspects, the nucleic acid is within a cell. In some embodiments where the nucleic acid is within a cell, the cell expresses a polypeptide encoded by the nucleic acid, where the polypeptide comprises at least 138 contiguous amino acids of SEQ ID NO: 7 or a unique subsequence of SEQ ID NO: 7.

The invention provides recombinant soybean plants that carry a recombinant nucleic acid of the invention. In some aspects, the recombinant nucleic acid results in a recombinant plant that is more resistant to at least one of soybean mosaic virus, frogeye leaf spot and brown stem rot than an isogenic soybean plant not comprising the recombinant nucleic acid. In some aspects, the recombinant nucleic acid encodes a polypeptide comprising chitinase activity. The recombinant nucleic acid used to create the recombinant plant can comprise, for example, (a) a polynucleotide corresponding to SEQ ID NO: 1 (SSLP039); (b) a polynucleotide corresponding to SEQ ID NO: 2 (SSLP090); (c) a unique subsequence of (a) or (b); (d) a polynucleotide that hybridizes under stringent conditions to the nucleic acid of (a) that is a polynucleotide sequence other than a sequence encoded by GenBank Accession Number AB006748, AB007126, AB007127 or AF402603; (e) a polynucleotide that is at least 70% identical to a nucleic acid of (a) that is a polynucleotide sequence other than a sequence encoded by GenBank Accession Number AB006748, AB007126, AB007127 or AF402603; (f) a polynucleotide that hybridizes under stringent conditions to the nucleic acid of (b); (g) a polynucleotide that is at least 70% identical to a polynucleotide of (b); and (h) a polynucleotide complementary to a polynucleotide of (a)-(g).

The invention also provides novel polypeptides. These polypeptides find a variety of uses, for example, they can provide disease-resistance to a transgenic plant when expressed in the plant, or alternatively, the polypeptides can be used to raise antibody, where the antibody is used to detect the absence or presence of a polypeptide marker in a plant sample. The isolated polypeptides of the invention can include: (a) an amino acid sequence of SEQ ID NO: 7 (SSLP039); (b) an amino acid sequence of SEQ IN NO: 9 (SSLP090); (c) a unique subsequence of (a) or (b); (d) an amino acid sequence encoded by the polynucleotide of SEQ ID NO: 1 (SSLP039); (e) an amino acid subsequence of at least 138 contiguous amino acids of (a) or (d); and, (f) an amino acid sequence encoded by a polynucleotide that hybridizes under stringent conditions over substantially the entire length of a polynucleotide of SEQ ID NO: 1, where the polynucleotide that hybridizes over substantially the entire length of a polynucleotide of SEQ ID NO: 1 is a polynucleotide sequence other than a sequence encoded by GenBank Accession Number AB006748, AB007126 or AB007127. In some aspects, the polypeptide comprises chitinase activity. In some aspects, the polypeptide is a fusion polypeptide; in some aspects the polypeptide comprises a tag sequence.

In some aspects, the invention provides a cell comprising at least one exogenous nucleic acid, where the exogenous nucleic acid encodes a polypeptide of the invention, as described above. The invention also provides antibodies that specifically bind a polypeptide of the inveniton. These antibodies can be monoclonal antibodies or polyclonal serum. The invention also provides an isolated polypeptide that is specifically bound by an antibody of the invention.

Definitions

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, include plural referents unless the content clearly dictates otherwise. Thus, for example, reference to "plant," "the plant" or "a plant" also includes a plurality of plants; use of the term "a nucleic acid" includes, as a practical matter, many copies of that nucleic acid molecule; similarly, the term "a probe" encompasses many probe molecules.

Unless otherwise indicated, nucleic acids are written left to right in 5' to 3' orientation, and amino acid sequences are written left to right in amino (N-terminus) to carboxy (C-terminus) orientation. Amino acid sequences provided herein use either standard one or three letter abbreviations for the amino acids, as commonly used in the art. Numeric ranges recited within the specification are inclusive of the numbers defining the range and include each integer or any non-integer fraction within the defined range.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The terms "marker," "molecular marker" or "marker nucleic acid" refer to a nucleotide sequence used as a point of reference when identifying a genetically linked loci. A marker can be derived from genomic nucleotide sequence or from expressed nucleotide sequences (e.g., from a cDNA). The term also refers to nucleic acid sequences complementary to the marker sequences, such as nucleic acids used as probes or primer pairs capable of amplifying the marker sequence.

In the context of this invention, a marker can be "associated with" another marker or some other genetic locus (for example, a disease-resistance locus), where the marker pair or the maker and second locus are genetically linked on the same linkage group and are in linkage disequilibrium (the marker nucleic acid and the trait are found together in progeny plants more frequently than if the nucleic acid and phenotype segregated separately). The term "linkage disequilibrium" refers to a non-random segregation of genetic loci. This implies that such loci are in sufficient physical proximity along a length of a chromosome that they tend to segregate together with greater than random frequency. The term "genetically linked" refers to genetic loci that are in linkage disequilibrium and statistically determined not to assort independently. Genetically linked loci cosegregate more than 50% of the time, e.g., from 51% to 100% of the time.

In the context of the present invention, a molecular marker that is genetically linked to another locus means that the marker and the second locus are on the same linkage group and typically within about 10 centiMorgans (cM) of each other. For example, an EST-derived molecular marker of the present invention is associated with a phenotypic trait such as resistance to a plant pathogen if the marker and the resistance allele at the gene locus are not more than 10 cM apart on the same linkage group, or more preferably, not more than 5 cM apart, or more preferably still, not more than 1 cM apart. In one preferred embodiment of the invention, the marker of the invention is derived from an expressed nucleic acid that is a resistance locus allele.

The term "homologous" refers to nucleic acid sequences that are derived from a common ancestral gene through natural or artificial processes (e.g., are members of the same gene family), and thus, typically share sequence similarity. Typically, homologous nucleic acids have sufficient sequence identity that one of the sequences or a subsequence thereof or its complement is able to selectively hybridize to the other under selective (e.g., stringent) hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing nucleic acid sequences typically have about at least 70% sequence identity, preferably at least 80% sequence identity, and most preferably 90%, 95%, 97%, 99%, or 100% sequence identity with each other. A nucleic acid that exhibits at least some degree of homology to a reference nucleic acid can be unique or identical to the reference nucleic acid or its complementary sequence.

The term "isolated" refers to material, such as polynucleotides or polypeptides, which are identified and separated from at least one contaminant with which it is ordinarily associated in its natural or original source. Furthermore, an isolated polynucleotide or polypeptide is typically present in a form or setting that is different from the form or setting that is normally found in nature. In preferred embodiments, the isolated molecule is substantially free from components that normally accompany or interact with it in its naturally occurring environment. In some embodiments, the isolated material optionally comprises material not found with the material in its natural environment, e.g., in a cell.

As used herein, the terms "exogenous" or "heterologous" as applied to polynucleotides or polypeptides refers to molecules that have been artificially supplied to a biological system (e.g., a plant cell, a plant gene, a particular plant species or a plant chromosome under study) and are not native to that particular biological system. The terms indicate that the relevant material originated from a source other than the naturally occurring source, or refers to molecules having a non-natural configuration, genetic location or arrangement of parts. The terms "exogenous" and "heterologous" are sometimes used interchangeably with "recombinant."

In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

The term "recombinant" indicates that the material (e.g., a recombinant nucleic acid, gene, polynucleotide or polypeptide) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from it natural text and cloned into any type of artificial nucleic acid vector. Protocols and reagents to produce recombinant molecules, especially recombinant nucleic acids, are common and routine in the art (see, e.g., Maniatis et al. (eds.), Molecular Cloning: A Laboratory Manual, Cold Spring Harbor Laboratory Press, NY, [1982]; Sambrook et al. (eds.), Molecular Cloning: A Laboratory Manual, Second Edition, Volumes 1-3, Cold Spring Harbor Laboratory Press, NY, [1989]; and Ausubel et al. (eds.), Current Protocols in Molecular Biology, Vol. 1-4, John Wiley & Sons, Inc., New York [1994]). The term recombinant can also refer to an organism that harbors a recombinant material, e.g., a plant that comprises a recombinant nucleic acid is considered a recombinant plant. In some embodiments, a recombinant organism is a transgenic organism.

The term "introduced" when referring to a heterologous or exogenous nucleic acid refers to the incorporation of a nucleic acid into a eukaryotic or prokaryotic cell using any type of suitable vector, e.g., naked linear DNA, plasmid, plastid or virion), converted into an autonomous replicon, or transiently expressed (e.g., transfected mRNA). The term includes such nucleic acid introduction means as "transfection," "transformation" and "transduction."

The term "host cell" means a cell that contains a heterologous nucleic acid, such as a vector, and supports the replication and/or expression of the nucleic acid. Host cells may be prokaryotic cells such as $E. coli$, or eukaryotic cells such as yeast, insect, amphibian or mammalian cells. Preferably, host cells are plant cells. In the context of the invention, one particularly preferred host cell is a soybean host cell.

The term "transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

Plant cell, as used herein includes, without limitation, cells within or derived from, for example and without limitation, plant seeds, plant tissue suspension cultures, plant embryos, meristematic tissue, callus tissue, leaves, roots, shoots, gametophytes, sporophytes, pollen and microspores.

The term "crossed" or "cross" in the context of this invention means the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

The term "introgression" refers to the transmission of a desired allele of a genetic locus from one genetic background to another. For example, introgression of a desired allele at a specified locus can be transmitted to at least one progeny plant via a sexual cross between two parent plants, at least one of the parent plants having the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a gene allele that imparts resistance to a plant pathogen.

As used herein, the term "isogenic" refers to two or more genetically identical (or nearly genetically identical, e.g., near-isogenic) organisms (e.g., two isogenic plants). Two isogenic individuals will typically originate from the same inbred strain. Isogenic individuals are typically homozygous at all or most genetic loci.

As used herein, the term "gene" is a sequence of nucleotide bases located in a particular position on a particular chromosome that encode a trait or product. A gene optionally comprises various parts, that when operably combined in either a native or recombinant manner, provide some product or trait. The term "gene" is to be interpreted broadly herein, encompassing mRNA, cDNA, cRNA and genomic DNA forms of a gene. In some cases, genes comprise coding sequences (an open reading frame) necessary for the production of a polypeptide. In addition to the coding region of the polynucleotide, the term "gene" can also optionally encompass non-coding regulatory sequences that reside at a genetic locus. Genes are frequently named for the phenotype that they control or affect, for example, a disease-resistance gene.

As used herein, an allele is one of the two or more alternative forms of a gene occupying the same locus on a particular chromosome or linkage group and differing from other alleles at the locus at one or more polymorphic sites. For example, a plant disease resistance locus on a plant linkage group can comprise one of two or more alleles. One or more of these alleles may impart disease resistance, while other alleles of that same gene may not provide disease resistance.

As used herein, "disease resistance" is the relative susceptibility of a plant to a disease. A plant disease is a dysfunction of normal physiological plant processes. A plant disease can be cause by microorganisms or abiotic factors. Those microorganisms that cause plant disease represent a wide variety of pathogens, including bacteria, fungi, nematodes and viruses. Disease resistance is relative, and can be absolute resistance to an infection, or can be partial or incomplete resistance. Furthermore, disease resistance can be narrow (resistance to only one species of a pathogen) or broad (resistant to many species of related pathogens, resistant to a particular type of infection or resistant to many varied types of pathogens).

As used herein, the term "vector" is used in reference to polynucleotide or other molecules that transfer nucleic acid segment(s) into a cell. The term "vehicle" is sometimes used interchangeably with "vector." A vector optionally comprises parts which mediate vector maintenance and enable its intended use (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses. A "cloning vector" or "shuttle vector" or "subcloning vector" contains operably linked parts which facilitate subcloning steps (e.g., a multiple cloning site containing multiple restriction endonuclease sites).

The term "expression vector" as used herein refers to a vector comprising operably linked polynucleotide sequences that facilitate expression of an operably linked coding sequence in a particular host organism (e.g., a bacterial expression vector or a plant expression vector). Polynucleotide sequences that facilitate expression in prokaryotes typically include, e.g., a promoter, an operator (optional), and a ribosome binding site, often along with other sequences. Eukaryotic cells can use promoters, enhancers, termination and polyadenylation signals and other sequences that are generally different from those used by prokaryotes.

As used herein, the term "amplification" or "amplifying" refers generally to any process that results in an increase in the copy number of a molecule or set or related molecules. As it applies to polynucleotide molecules, amplification means the production of multiple copies of a polynucleotide molecule, or part of a polynucleotide molecule, from one or few copies or small amounts of starting material. Amplification of polynucleotides encompasses a variety of chemical and enzymatic processes. The generation of multiple DNA copies from one or a few copies of a template DNA molecule during a polymerase chain reaction (PCR) or a ligase chain reaction (LCR) are forms of amplification. Amplification is not limited to the strict duplication of the starting molecule. For example, the generation of multiple RNA molecules from a single DNA molecule during the process of transcription (e.g., in vitro transcription) is a form of amplification.

In some embodiments, amplification is optionally followed by additional steps, for example, but not limited to, labeling, sequencing, purification, isolation, hybridization, size resolution, expression, detecting and/or cloning.

As used herein, the term "polymerase chain reaction" (PCR) refers to a method for amplification well known in the art for increasing the concentration of a segment of a target polynucleotide in a sample, where the sample can be a single polynucleotide species, or multiple polynucleotides. Generally, the PCR process consists of introducing a molar excess of two or more extendable oligonucleotide primers to a reaction mixture comprising the desired target sequence(s), where the primers are complementary to opposite strands of the double stranded target sequence. The reaction mixture is subjected to a program of thermal cycling in the presence of a DNA polymerase, resulting in the amplification of the desired target sequence flanked by the DNA primers. Reverse transcriptase PCR (RT-PCR) is a PCR reaction that uses RNA template and a reverse transcriptase to first generate a single stranded DNA molecule prior to the multiple cycles of DNA-dependent DNA polymerase primer elongation. Multiplex PCR refers to PCR reactions that produce more than one amplified product in a single reaction, typically by the inclusion of more than two primers in a single reaction. Methods for a wide variety of PCR applications are widely known in the art, and described in many sources, for example, Ausubel et al. (eds.), Current Protocols in Molecular Biology, Section 15, John Wiley & Sons, Inc., New York (1994).

As used herein, the term "in vitro" refers to an artificial environment and to processes or reactions that occur within the artificial environment. The term "in vivo" refers to a natural environment (e.g., in a plant or in a plant cell) and to processes or reactions that occur within a natural environment. The term "in situ" is used to describe a process typically for detecting the presence of something in its natural environment or cellular location using exogenously supplied reagents. The sample being analyzed is typically a cytological preparation (e.g., cells, tissues or organs), but can also be, for example, intact chromosomes. For example, an in situ hybridization is a hybridization reaction where a nucleic acid probe can be used to detect RNA within a cell or tissue cross section in order to identify the subcellular location or region of localized RNA expression. Also, fluorescence in situ hybridization (FISH) can be used to identify a linkage group and approximate genetic locus of a particular polynucleotide sequence.

As used herein, the term "base" refers to any nitrogen-containing heterocyclic moiety capable of forming Watson-Crick hydrogen bonds in pairing with a complementary base or base analog. A large number of bases, base analogs and base derivatives are known. Examples of bases include purines and pyrimidines, and modified forms thereof. The naturally occurring bases include adenine (A), guanine (G), cytosine (C), uracil (U), and thymine (T), and analogs thereof. As used herein, it is not intended that the invention be limited to naturally occurring bases, as a large number of unnatural (non-naturally occurring) bases and their respective unnatural nucleotides that find use with the invention are known to one of skill in the art.

The term "nucleoside" refers to a compound consisting of a base linked to the C-1' carbon of a sugar, for example, ribose or deoxyribose.

The term "nucleotide" refers to a phosphate ester of a nucleoside, as a monomer unit or within a polynucleotide. "Nucleotide 5'-triphosphate" refers to a nucleotide with a triphosphate ester group at the 5' position, and are sometimes denoted as "NTP", or "dNTP" and "ddNTP." A modified nucleotide is any nucleotide (e.g., ATP, TTP, GTP or CTP)

that has been chemically modified, typically by modification of the base moiety. Modified nucleotides include, for example but not limited to, methylcytosine, 6-mercaptopurine, 5-fluorouracil, 5-iodo-2'-deoxyuridine and 6-thioguanine.

The terms "nucleic acid," "polynucleotide," "nucleic acid sequence," "polynucleotide sequence," "oligonucleotide," "oligomer" or "oligo" as used herein refers to a polymeric arrangement of monomers that can be corresponded to a sequence of nucleotides, e.g., a DNA, RNA, peptide nucleic acid, or the like. A polynucleotide can be single- or double-stranded, and can be complementary to the sense or antisense strand of a gene sequence, for example. A polynucleotide can hybridize with a complementary portion of a target polynucleotide to form a duplex, which can be a homoduplex or a heteroduplex. The length of a polynucleotide is not limited in any respect. Linkages between nucleotides can be internucleotide-type phosphodiester linkages, or any other type of linkage. A "polynucleotide sequence" refers to the sequence of nucleotide monomers along the polymer. A polynucleotide can be enzymatically extendable or enzymatically non-extendable. Unless otherwise indicated, a particular polynucleotide sequence of the invention optionally encompasses complementary sequences, in addition to the sequence explicitly indicated.

Polynucleotides that are formed by 3'-5' phosphodiester linkages are said to have 5'-ends and 3'-ends because the nucleotide monomers that are reacted to make the polynucleotide are joined in such a manner that the 5' phosphate of one mononucleotide pentose ring is attached to the 3' oxygen (hydroxyl) of its neighbor in one direction via the phosphodiester linkage. Thus, the 5'-end of a polynucleotide molecule has a free phosphate group or a hydroxyl at the 5' position of the pentose ring of the nucleotide, while the 3' end of the polynucleotide molecule has a free phosphate or hydroxyl group at the 3' position of the pentose ring. Within a polynucleotide molecule, a position or sequence that is oriented 5' relative to another position or sequence is said to be located "upstream," while a position that is 3' to another position is said to be "downstream." This terminology reflects the fact that polymerases proceed and extend a polynucleotide chain in a 5' to 3' fashion along the template strand. Unless denoted otherwise, whenever a polynucleotide sequence is represented, it will be understood that the nucleotides are in 5' to 3' orientation from left to right. A "polynucleotide" is not limited to any particular length or range of nucleotide sequence, as the term "polynucleotide" encompasses polymeric forms of nucleotides of any length.

As used herein, it is not intended that the term "polynucleotides" be limited to naturally occurring polynucleotides, naturally occurring backbones or naturally occurring internucleotide linkages. One familiar with the art knows well the wide variety of polynucleotide analogues, unnatural nucleotides, non-natural phosphodiester bond linkages and internucleotide analogs that find use with the invention. Non-limiting examples of such unnatural structures include non-ribose sugar backbones, 3'-5' and 2'-5' phosphodiester linkages, internucleotide inverted linkages (e.g., 3'-3' and 5'-5'), branched structures, and internucleotide analogs (e.g., peptide nucleic acids (PNAs), locked nucleic acids (LNAs), $C_1$-$C_4$ alkylphosphonate linkages such as methylphosphonate, phosphoramidate, $C_1$-$C_6$ alkyl-phosphotriester, phosphorothioate and phosphorodithioate internucleotide linkages. Furthermore, a polynucleotide may be composed entirely of a single type of monomeric subunit and one type of linkage, or can be composed of mixtures or combinations of different types of subunits and different types of linkages (a polynucleotide can be a chimeric molecule). As used herein, a polynucleotide analog retains the essential nature of natural polynucleotides in that they hybridize to a single-stranded nucleic acid target in a manner similar to naturally occurring polynucleotides.

As used herein, the terms "complementary" or "complementarity" are used in reference to antiparallel strands of polynucleotides related by the Watson-Crick and Hoogsteen-type base-pairing rules. For example, the sequence 5'-AGTTC-3' is complementary to the sequence 5'-GAACT-3'. The terms "completely complementary" or "100% complementary" and the like refer to complementary sequences that have perfect Watson-Crick pairing of bases between the antiparallel strands. The terms "partially complementary," "incomplete complementarity" or "incompletely complementary" and the like refer to any alignment of bases between antiparallel polynucleotide strands that is less than 100% perfect (e.g., has mismatches).

As used herein, the term "probe" refers to a polynucleotide that is capable of hybridizing to a nucleic acid of interest, and typically is labeled with any suitable "reporter molecule" so that the probe is detectable. Detection systems include, but are not limited to, the detection of enzymatic activity, fluorescence, radioactivity, luminescence or binding properties that permit specific binding of the reporter (e.g., where the reporter is an antibody). It is not intended that the present invention be limited to any particular probe, label or detection system. The source of the polynucleotide used in the probe is not limited, and can be produced synthetically, in vitro, or can be a subsequence of a larger nucleic acid molecule isolated from a cell (e.g., a bacterial cell). A PCR primer or PCR primer pair can be a probe for the detection of a target polynucleotide.

As used herein, the terms "peptide," "polypeptide" and "protein" all refer to a primary sequence of amino acids that are typically (but not necessarily) joined by covalent "peptide linkages." A polypeptide is characterized by its amino acid sequence (its primary structure). In general, a peptide consists of a few amino acids, typically from 2-25 amino acids, and is shorter than a protein. The term "polypeptide" encompasses amino acid polymers of any length, including both peptides and proteins. A polypeptide can be of any type and from any source, including but not limited to, a naturally occurring molecule, a recombinant molecule, a synthetic or naturally occurring peptide, and may refer to a subsequence portion of a larger polypeptide. It is not intended that polypeptides of the invention be limited to full-length, native polypeptide sequences associated with a particular biological activity.

As used herein, the terms "subsequence," "fragment" or "portion" or the like refer to any portion of a larger sequence (e.g., a polynucleotide or polypeptide sequence), up to and including the complete sequence. The minimum length of a subsequence is generally not limited, except that a minimum length may be useful in view of its intended function. For example, a polynucleotide subsequence can be used as a PCR primer, as a nucleic acid hybridization probe, or as an open reading frame that encodes a polypeptide (e.g., a chitinase polypeptide). Thus, the polynucleotide subsequence should be long enough to serve as a PCR primer, be long enough to specifically hybridize to a target sequence, or be long enough to encode a polypeptide having chitinase activity; respectively. Polynucleotide subsequences of the invention can be any length, for example, at least 10, 15, 20, 50, 100 or 200 nucleotides or more in length.

Similarly, the minimum length of a polypeptide subsequence is generally not limited, except that a minimum length may be useful in view of its intended function. For example, a polypeptide subsequence can be used as antigenic material to produce an antibody, or can be produced from an open reading frame in a host cell to impart disease resistance to a transgenic plant. Thus, the polypeptide subsequences should be long enough to solicit an immune response (e.g., can act an immunogen), or should be long enough to contain chitinase activity; respectively. Polypeptide subsequences of the invention can be, for example, at least 5, 10, 20, 50, 100 or 200 amino acids or more in length.

The term "unique subsequence" refers to a polynucleotide or polypeptide subsequence that is unique as compared to a polynucleotide or polypeptide sequence derived from any of NCBI GenBank Accession Numbers AB006748, AB007126, AB007127; BAA77675, BAA77676, BAA77677 or AF402603. The unique subsequence has at least one unique nucleotide or amino acid position that distinguishes the sequence from those sequences provided in the GenBank submissions listed above.

BRIEF DESCRIPTION OF THE FIGURES

FIGS. 1A through 1D provide a table summarizing the marker allele analysis from approximately 114 recombinant inbred soybean lines for eight framework markers on linkage group D1b, four framework markers on linkage group J, the SSLP039 and SSLP090 EST markers, three additional SSLP EST markers, and one resistance gene analogue (RGA) locus.

DETAILED DESCRIPTION

Figure 2:
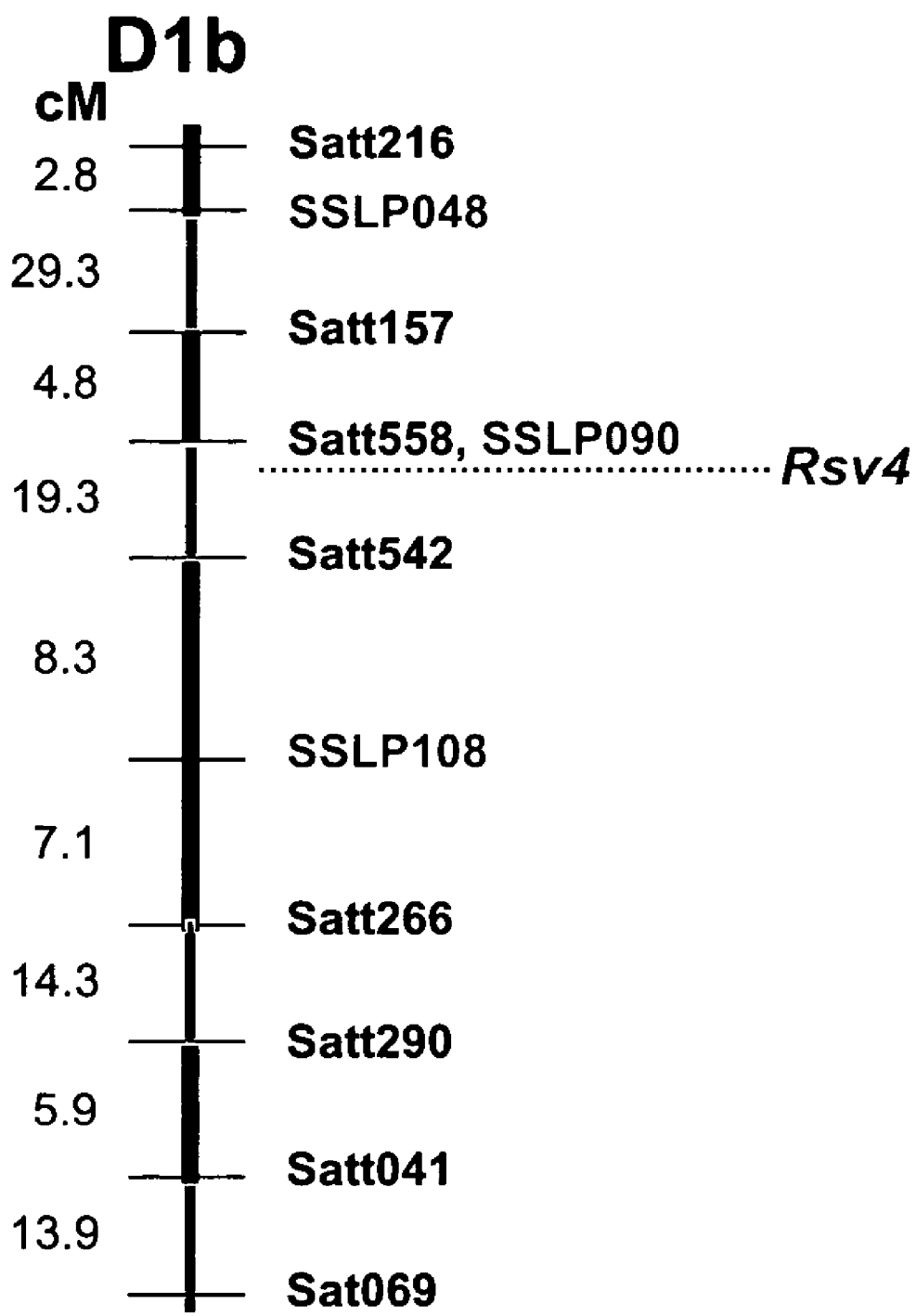
FIG. 2 provides a genetic linkage map for soybean linkage group D1b. EST markers SSLP048, SSLP090 and SSLP108 are indicated on the map.

Efforts to improve soybean as a crop can benefit tremendously from the improvement of molecular marker techniques. What is needed are new, high through-put markers that are easily incorporated into the available soybean genetic map information, and furthermore, are linked to known disease-resistance loci to facilitate marker assisted selection (MAS) of resistant plants. The present invention meets this need by exploiting ESTs to produce two molecular markers that are linked to known disease resistance genes.

The present invention relates to the identification and use of novel EST-derived soybean genetic markers, and in particular, markers that are linked to known disease-resistance genetic loci in *Glycine* sp. The invention encompasses the nucleic acids corresponding to (or derived from) these EST sequences, including but not limited to probes, amplification primers and amplification products, all of which are useful, for example, in the genotyping of plants. The markers of the invention are used to identify soybean plants that are resistant or exhibit improved resistance to various soybean pathogens. Accordingly, these markers are useful for marker-assisted selection (MAS) and breeding of disease resistant plants, and identification of susceptible or resistant plants. More generally, these markers are useful in the saturation of markers on soybean genetic map.

A number of soybean genetic loci have been previously identified that correlate with resistance to various plant pathogens. Of particular interest are those loci that map close to (for example, are within 10 cM of) the SSLP EST markers provided by the present invention. A listing of these loci is provided in Table 3, and further discussed below.

Soybean Mosaic Virus Resistance Gene 4 (Rsv4)

Soybean mosaic virus (SMV; Genus *Potyvirus*; Family Potyviridae), the causal agent of soybean mosaic, occurs worldwide and is one of the most economically significant pathogens in soybean (*Glycine max* [L.] Merrill). SMV causes significant yield losses reaching in some cases as high as 94% of total yield. Infection of plants at an early stage results in reduction of pod set, reduction in seed size and weight, increase in seed coat mottling and decrease in seed quality. If potyviruses occur in combination with other unrelated viruses, the effects on yield quantity and quality are more severe. Plants infected by potyviruses are also more susceptible to fungal pathogens. SMV causes up to 40% yield loss when plants are infected at or before floral development.

Resistance to SMV in soybeans has been detected in various cultivars. Molecular and genetic studies of resistant cultivars have revealed the presence of genes for resistance to SMV, which have been mapped to multiple genomic regions. One of these genes, termed Rsv4, is completely dominant and confers resistance in both the homozygous and the heterozygous conditions and is non-necrotic (Ma et al., *Theor. Appl. Genet.*, 91:907-914 [1995]). Rsv4 has been mapped to molecular linkage group (MLG) D1b (Hayes et al., *Crop Science* 40:1434-1437 [2000]; Hayes et al., *Theor. Appl. Genet.*, 101:789-795 [2000]). The molecular identity of this gene remains unknown.

Frogeye Leaf Spot Resistance Gene (Rcs3)

Frogeye leaf spot (FLS) (caused by the fungus *Cercospora sojina* Hara) is a foliar disease of soybean (*Glycine max* (L.) Merrill) that causes significant yield loss and poor seed quality in southeastern USA as well as worldwide. The disease can cause 10-50% yield loss, with losses as high as 60% and greater reported in tropical environments such as Nigeria. Resistant cultivars are known, and genetic studies have identified at least three resistance loci in American strains. One of these resistance genes, termed Rcs3, has been reported to condition resistance to all known races of *C. sojina*. Molecular mapping of the Rcs3 locus has placed the gene on linkage group J (Yang et al., *Plant Breeding* 120:73-78 [2001]).

Brown Stem Rot Resistance Genes (Rbs1, Rbs2 and Rbs3)

Brown stem rot (BSR) of soybean [*Glycine max* (L.) Merrill] is caused by the fungal pathogen *Phialophora gregata*. Brown stem rot is widespread in Canada and in the midwest and southeast United States. Yield losses up to 25% may occur primarily through the reduction in number and size of seeds. Brown stem rot resistance genes Rbs1, Rbs2, and Rbs3 have been identified in soybean through traditional genetic analysis. Although brown stem rot resistance is widely utilized and prevents some yield loss in soybean, selection for this trait is laborious and confounded by environmental variation. Identification of molecular markers linked to the Rbs loci will improve efficiency of selection for brown stem rot resistance. Mapping analysis has placed a cluster of BSR resistance loci, including Rbs1, Rbs2 and Rbs3 on linkage group J of the soybean molecular map (Bachman et al., *Crop Science* 41:527-535 [2001]; Shoemaker et al., 2003, Soybase class browser: Pathology. Iowa: Iowa State University, http://soybase.ncgr.org/cgi-bin/ace/generic/search/soybase).

In addition to their use in marker assisted selection for disease-resistance traits, the genetic markers of the invention are also used to identify and isolate (e.g., clone) the genomic loci that include the disease-resistance gene, for example, by positional cloning. In addition, in the case where the EST marker is derived from the expressed gene that imparts the disease resistance, a full length cDNA can be isolated. Isolation of the disease resistance loci by either positional genomic cloning or identification of a full-length cDNA allows the production of transgenic cells and plants exhibiting improved pathogen resistance.

EST Library Creation and Identification of Candidate Markers

A total of 71 soybean EST libraries were constructed using mRNA isolated from a variety of plant tissues, including developing seed, leaves, roots, stem, immature flower, and plant embryo. Some of the plants that were used to construct the EST libraries were challenged with various pathogens such as SCN, *Sclerotinia* (white mold) and severe stunt virus. The libraries were constructed using well-established procedures.

The 71 EST libraries collectively yielded approximately 194,000 EST sequences. These 194,000 EST sequences were BLASTed against known "disease-related plant sequences (including known disease-resistance protein motifs and disease-response genes induced or upregulated in response to infection) to identify approximately 25,000 EST sequences of interest. These 25,000 ESTs were further examined to reduce redundancy, thereby identifying 1218 disease-related EST marker candidates. PCR primers for approximately 200 of the 1218 candidates were designed and produced. Approximately 50 of these candidates were mapped onto the soybean molecular linkage groups.

Based on their map locations and/or primary sequences, two of the mapped ESTs were of particular interest, namely, SSLP039 and SSLP090. These two ESTs were both isolated from a library generated from immature flower tissue isolated from a "Wye" soybean culitvar that was not challenged with any pathogen. The EST SSLP039 demonstrates strong homology to a known disease resistance gene.

Ideally, in a most preferred embodiment, the EST nucleotide sequences correspond to mRNA sequences that produce polypeptide products encoded by a disease resistance loci. In this embodiment, the markers derived from these EST sequences map to the same genetic position as the previously identified disease-resistance loci. Furthermore, these EST markers can be used as probes to identify and isolate a full length expressed gene (or a genomic sequence) that encodes the polypeptide that results in disease resistance. These nucleotide sequences can then be used to create populations of transgenic plants that carry an exogenous copy of the disease resistance gene.

In other embodiments, the EST sequences are not derived from the disease resistance locus, but rather, are derived from sequences that are linked to the disease resistance loci. Any marker that is linked to a resistance gene can be used in marker assisted selection of resistant plants.

EST library sequences were scanned as described in EXAMPLE 1 and two candidate makers were identified. Selection of EST sequences for further analysis was based on various criteria. First, EST sequences that have open reading frames that are predicted to encode biological activities that may impart disease resistance were candidates for further mapping analysis. For example, SSLP039 is predicted to encode an acidic chitinase that may potentially provide resistance to pathogens having chitinous cell walls, including fungi (discussed in more detail below; see EXAMPLE 1).

A second criteria for selection of the molecular markers was the likely presence of polymorphism, as identified by the BLAST searches described in EXAMPLE 1. The polymorphism search included not only the simple sequence repeats of SSR-type heterogeneity, but also included the broader family of simple sequence length polymorphism (SSLP). This type of polymorphism can include insertion and deletion variability as well as simple sequence repeats, thereby expanding the potential number of useful markers that might be harvested from the EST information.

The identification of SSLP-type loci is advantageous over SSRs because it utilizes more sequence information to search for polymorphism. Thus, SSLPs result in the development of more useful markers. The present invention provides soybean markers that would have remained undiscovered had the marker criteria been limited to SSR-type heterogeneity.

The markers of the present invention take advantage of the heterogeneity of gene alleles in the identification of suitable molecular markers. In general, SSLP can include the SSR-type variability of high levels of di-, tri-, or tetra-nucleotide tandem repeats, as well as other types of insertion or deletion events. Dinucleotide repeats have been reported to occur in the human genome as many as 50,000 times with number of repeats varying from 10 to 60 or more (Jacob et al. (1991) *Cell* 67:213). Dinucleotide repeats have also been found in higher plants (Condit and Hubbell (1991) *Genome* 34:66).

One result of this heterogeneity is differences in size of a particular genetic region (or in an expressed sequence). In one embodiment, the heterogeneity data is generated (e.g., visualized) by hybridizing primers to conserved regions flanking the variable region. PCR is then used to amplify the region between the primers. The amplified sequences are then electrophoresed and visualized by any suitable method. When using EST-derived markers as provided in the present invention, differences in amplicon size is indicative of different gene alleles, and is characteristic and reproducible for that allele. In some embodiments, the size of the PCR amplicon is determined simply by resolving the products of the PCR reaction on an agarose gel and visualizing the amplicons using a radiolabel that was included on one of the PCR primers.

Candidate EST nucleotide sequences were queried against the public NCBI soybean EST database using the BLAST search tool. The search results were scanned for SSR and insertion/deletion mutations that may produce favorable marker polymorphism at that locus in different soybean genomes (lines). Two EST marker candidates were identified as having potential heterogeneity, and were chosen for further mapping analysis; SSLP039 and SSLP090. The SSLP039 cDNA EST generated 532 nucleotides of sequence information (SEQ ID NO: 1), while the SSLP090 EST had 412 nucleotides of sequence information (SEQ ID NO: 2).

The two SSLP markers were used to perform a diversity analysis on the twelve soybean lines shown in Table 1. This analysis was conducted as described in EXAMPLES 4 and 5. The EST markers were able to detect at least two alleles of the SSLP039 marker, and at least six alleles of the SSLP090 marker. This polymorphism made these markers suitable candidates for mapping analysis.

Superimposing Disease Resistance LOCI onto the Skeletal Map

An integrated, globally edifying "skeletal" genetic linkage map of the soybean genome incorporating a large set of easily reproducible SSR markers mapped in three different populations has been produced (Cregan et al. *Crop Sci.*, 39:1464-1490 [1999]). This published map permitted the integration of known disease resistance loci into the map by looking at the published mapping data for the various disease-resistance loci, and superimposing that information on the Cregan map. The use of known reproducible markers to construct the skeletal map allows the mapping discoveries of independent studies to be related by a common set of markers. As a result of integral maps, soybean has experienced improvements from marker-assisted selection for a variety of plant diseases.

The placement of various disease resistance loci on the soybean genetic map is summarized in Table 3, and described in EXAMPLE 9. As shown in the table, each of the resistance genes Rsv4, Rcs3, Rbs1, Rbs2 and Rbs3 are known to be associated with (linked to) previously characterized SSR markers. As a result, mapping these marker SSR's permits the placement of the various disease resistance loci on the genetic map.

Mapping of Novel EST Molecular Markers and Sequence Analysis

The genomic map locations of SSLP030 and SSLP090 were determined as described EXAMPLES 8 and 9. Using recombinant inbred lines (RILs), the two EST markers were assigned to linkage groups and mapped relative to known SSR markers already placed on the map. This mapping data showing the inheritance of the marker alleles in the RILs as well as the inheritance patterns of the framework markers is shown in FIGS. 1A through 1D.

With the map positions of the SSLP039 and SSLP090 markers determined, the correlation of the two SSLP markers to known disease loci was inferred. The analysis revealed that the SSLP039 locus resides on linkage group J, and maps to approximately the same map position as SSR marker Satt244. Since it has previously been shown that Satt244 maps approximately 1.1 cM from the Rcs3 locus (Yang et al., *Plant Breeding* 120:73-78 [2001]), it is inferred that SSLP039 also maps closely to the Rcs3 locus. From the mapping data provided herein, it can also be inferred that SSLP039 maps in close proximity to the Rbs resistance loci cluster.

This analysis also revealed that the SSLP090 locus resides on linkage group D1b, and maps in the vicinity of markers Satt558 and Satt542. Since it has previously been shown that Satt542 maps approximately 4.7 cM from the locus and 7.8 cM from the Satt558 locus (Hayes et al., *Crop Science* 40:1434-1437 [2000]; Hayes et al., *Theor. Appl. Genet.*, 101: 789-795 [2000]), it is inferred that SSLP090 is also closely associated with the Rsv4 locus.

The map positions of SSLP039 and SSLP090 are in close proximity to known resistance gene loci. SSLP039 mapped to a region on the bottom of linkage group J near a cluster of disease resistance loci, including Rcs3, Rbs1, Rbs2 and Rbs3. SSLP090 mapped to the chromosomal region containing Rsv4, a gene that provides resistance to all known strains of soybean mosaic virus (SMV). The close genetic proximity of SSLP039 and SSLP090 to these known disease-resistance loci indicates that these EST markers can serve as linked markers in marker-assisted selection of disease-resistant plants.

SSLP039

Sequence analysis using the NCBI BLAST search tool revealed that the 532 nucleotide EST SSLP039 (SEQ ID NO: 1) encodes a novel polypeptide belonging to the chitinase family, which is known to destroy the cell walls of invading fungal pathogens. The 176 amino acids encoded by the SSLP open reading frame (SEQ ID NO: 7) are homologous, but not identical to, a known soybean ethylene-inducible acidic chitinase (Watanabe et al., *Biosci. Biotechnol. Biochem.*, 63(2): 251-256 [1999]; NCBI GenBank Accession Nos. AB006748, AB007126, AB007127; BAA77675, BAA77676 and BAA77677). Polynucleotide portions comprising at least 258 contiguous nucleotides of SEQ ID NO: 1 are unique with respect to the GenBank Accession number cited above. Similarly, polypeptide portions comprising at least 138 contiguous amino acids of SEQ ID NO: 7 are unique with respect to the GenBank Accession numbers cited above.

The present invention provides, for example, a novel nucleic acid (SEQ ID NO: 1), unique subsequences thereof, novel nucleic acids comprising the nucleic acid of SEQ ID NO: 1, novel portions of SEQ ID NO: 1 comprising at least 258 contiguous nucleotides, as well as other embodiments.

The invention also provides a novel polypeptide (SEQ ID NO: 7), unique subsequences of the polypeptide, novel portions comprising at least 138 contiguous amino acids of SEQ ID NO: 7, antibodies specific for a polypeptide encoded by SEQ ID NO: 1, as well as other embodiments.

The SSLP039 marker was mapped to a location approximately 1.1 cM from the Rcs3 locus, leaving open the possibility that the SSLP039 marker may be part of one of the resistance genes at the bottom of linkage group J, e.g., part of the open reading frame of Rcs3. The possibility that SSLP039 and Rcs3 are the same locus finds indirect support in the observation that the EST open reading frame encodes a polypeptide having homology to chitinase-family polypeptides. If the EST SSLP039 and Rcs3 are the same locus, the chitinase motif in SSLP039 would suggest a mechanism by which the Rcs3 gene may provide disease resistance. Chitinase proteins related to but not identical to the chitinase of the present invention are known to be directly involved with infection-resistance responses by breaking down the cell walls of fungal pathogens.

If the SSLP039 EST is the Rcs3 expressed sequence, or the expressed sequence of any of the expressed resistance genes on linkage group J, a full length cDNA can be easily isolated from a suitable cDNA library using techniques known to one of skill in the art, and are available in a variety of published sources, e.g., Sambrook et al. (eds.), Molecular Cloning: A Laboratory Manual, Second Edition, Volumes 1-3, Cold Spring Harbor Laboratory Press, NY, [1989]; and Ausubel et al. (eds.), Current Protocols in Molecular Biology, Vol. 1-4, John Wiley & Sons, Inc., New York [1994]). Once isolated, a full-length chitinase cDNA can be used to construct disease-resistant transgenic plants, as described below.

SSLP090

SSLP090 mapped to a location on chromosome D1b near the heretofore uncloned Rsv4 gene, which provides resistance to all strains of SMV. Thus, the SSLP090 EST provides a useful marker for tracking the Rsv4 gene and for use in marker-assisted selection. High-resolution mapping and chromosome walking methods can be employed to clone the Rsv4 gene, facilitated by identification of the SSLP090 marker provided by the present invention.

The sequencing of this cDNA EST generated 412 nucleotides of sequence information, provided in SEQ ID NO: 2. One of the six reading frames of this nucleotide sequence yielded translation of a novel 86 amino acid polypeptide (SEQ ID NO: 9), with a single methionine at position 14. This polypeptide shows limited homology to NAC domain protein NAC2, a putative transcription factor (NCBI GenBank Accession Number AF402603). Polynucleotide portions comprising at least 23 contiguous nucleotides of SEQ ID NO: 2 are unique with respect to the GenBank Accession number cited above. Similarly, polypeptide portions comprising at least 8 contiguous amino acids of SEQ ID NO: 9 are unique with respect to the GenBank Accession number cited above.

The present invention provides, for example, a novel nucleic acid (SEQ ID NO: 2), unique subsequences thereof, novel nucleic acids comprising the nucleic acid of SEQ ID NO: 2, novel portions of SEQ ID NO: 2 comprising at least 23 contiguous nucleotides, as well as other embodiments. The invention also provides novel polypeptides encoded by SEQ ID NO: 2, unique subsequences of the polypeptide, antibodies specific for a polypeptide encoded by SEQ ID NO: 2, as well as other embodiments.

Polynucleotides of the Invention

The present invention provides polynucleotides/nucleic acids having a variety of uses. It is not intended that the invention be limited to polynucleotide sequences recited herein, as one of skill in the art recognizes that polynucleotide subsequences (e.g., unique subsequences), and homologous polynucleotides, as taught herein, are also within the scope of the invention.

Making Polynucleotides

Polynucleotides of the invention can be prepared, for example, by standard solid-phase methods, according to known synthetic methods. Typically, fragments of up to about 100 bases are individually synthesized, then joined (e.g., by enzymatic or chemical ligation methods, or polymerase mediated recombination methods) to form essentially any desired continuous sequence. For example, the polynucleotides of the invention can be prepared by chemical synthesis using, e.g., the classical phosphoramidite method described by Beaucage et al., (1981) *Tetrahedron Letters* 22:1859-69, or the method described by Matthes et al., (1984) *EMBO J.* 3: 801-05., e.g., as is typically practiced in automated synthetic methods. According to the phosphoramidite method, polynucleotides are synthesized, e.g., in an automatic DNA synthesizer, and optionally purified, annealed, ligated, and/or cloned in appropriate vectors.

In addition, essentially any nucleic acid can be custom ordered from any of a variety of commercial sources, such as The Midland Certified Reagent Company, The Great American Gene Company, ExpressGen Inc., Operon Technologies Inc. (Alameda, Calif.) and many others. Similarly, peptides and antibodies can be custom ordered from any of a variety of sources, such as PeptidoGenic, HTI Bio-products, Inc., BMA Biomedicals Ltd (U.K.), Bio.Synthesis, Inc., and many others.

Polynucleotides of the invention can also be obtained by screening cDNA libraries to isolate at least one cDNA clone (e.g., a cDNA clone that encodes a polypeptide that has chitinase activity). Screening for cDNA sequences can utilize polynucleotide probes (e.g., a probe derived from SEQ ID NO: 1) that can hybridize to a cDNA); or alternatively, screening for suitable cDNA molecules can utilize a PCR amplification strategy using a single primer or a primer pair, e.g., the PCR primer pair of SEQ ID NOS: 3 and 4. The cDNA polynucleotides that can be identified in the screening using reagents provided herein will encode chitinase polypeptides and fragments of those polypeptides, or homologues thereof. Procedures for screening and isolating cDNA clones are well-known to those of skill in the art. Such techniques are described in numerous sources, for example, Sambrook et al. (1989) supra, and Ausubel et al. (1989) supra.

As described in more detail herein, the polynucleotides of the invention include sequences that encode novel chitinase enzymes and sequences complementary to the coding sequences, and novel fragments of coding sequence and complements thereof. The polynucleotides can be in the form of RNA or in the form of DNA, and include mRNA, cRNA, synthetic RNA and DNA, and cDNA. The polynucleotides can be double-stranded or single-stranded, and if single-stranded, can be the coding strand or the non-coding (antisense, complementary) strand. The polynucleotides optionally include the coding sequence of a chtinase enzyme (i) in isolation, (ii) in combination with additional coding sequence, so as to encode, e.g., a fusion protein, a pre-protein, a prepro-protein, or the like, (iii) in combination with non-coding sequences, such as introns, control elements such as a promoter, a terminator element, or 5' and/or 3' untranslated regions effective for expression of the coding sequence in a suitable host, and/or (iv) in a vector or host environment in which the interferon homologue coding sequence is a heterologous gene. Sequences can also be found in combination with typical compositional formulations of nucleic acids, including in the presence of carriers, buffers, adjuvants, excipients and the like.

Using Polynucleotides

The polynucleotides of the invention have a variety of uses. In one aspect, the invention provides nucleic acids that are used as primers, for example PCR marker primers such as those provided in SEQ ID NOS: 3 and 4, or SEQ ID NOS: 5 and 6, for the generation of the SSLP039 or SSLP090 marker amplicons, respectively.

In some aspects, the invention provides nucleic acids that can be used as probes. For example, a nucleic acid probe can be a probe that can specifically hybridize to a nucleotide sequence comprising the SSLP039 EST (SEQ ID NO: 1) or the SSLP090 EST (SEQ ID NO: 2) nucleotide sequence, or a portion of those sequences.

In some embodiments, the invention provides nucleic acids (e.g., SEQ ID NOS: 1 and 2) that encode polypeptides (SEQ ID NOS: 7 and 9, respectively). These polynucleotides, or portions of these polynucleotides, can be cloned into a suitable expression vector and expressed in a suitable host system to produce the respective polypeptide, or a portion of the polypeptide. The cloning of the polynucleotides of the invention into an expression vector for this purpose will result in larger nucleic acid molecules where the polynucleotides of the invention will be associated with and in operable combination with other heterologous polynucleotide elements. These heterologous polynucleotide elements control or enhance the expression of the polypeptide in a host cell system (or in vitro).

In one aspect, the polypeptide thus produced can be isolated and used as an immunogen in an animal to produce polypeptide-specific antibodies. In this aspect, the size of the polynucleotide used to expresses the polypeptide is not particularly limited, except that the fragment produces a polypeptide large enough to result in the generation of antibody specific for the polypeptide.

In some embodiments, the polynucleotides of the present invention (e.g., SEQ ID NO: 1) find use as probes to identify and isolate a full-length cDNA molecule corresponding to the cloned EST SSLP039.

In some embodiments, the expression vector comprising the polynucleotide that produces the polypeptide results in a polypeptide that has chitinase activity. In this embodiment, that expression vector finds use in the construction of transgenic plants that express chitinase activity, thereby resulting in plants resistant to various diseases.

It is not intended that polynucleotides of the invention (including subsequences, fragments, or portions, or any polynucleotide used in any method described herein) be limited to any particular minimum or maximum length. The minimum length of a polynucleotide is generally not limited, except that a minimum length may be useful in view of the polynucleotide's intended use. For example, a polynucleotide sequence of the invention can be used as a PCR primer, as a nucleic acid hybridization probe, a PCR amplicon, or as an open reading frame that encodes a polypeptide (e.g., a chitinase polypeptide). Thus, the polynucleotide sequence should be long enough, for example, to serve as a PCR primer, be long enough to specifically hybridize to a target sequence, or be long enough to encode a polypeptide having chitinase activity. Polynucleotide sequences of the invention can be any length, for example, at least 10, 15, 20, 50, 100 or 200 nucleotides or more in length.

Silent Variations

It will be appreciated by those skilled in the art that due to the degeneracy of the genetic code, a multitude of nucleic acid sequences encoding chitinase polypeptides of the invention may be produced, some which may bear minimal sequence homology to the nucleic acid sequences explicitly disclosed herein.

For instance, codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent substitutions," (also termed "wobble position" if the variable position is the last nucleotide of the codon) when they occur within the polynucleotides of the present invention, result in polynucleotide sequences that are within the scope of the present invention. One of skill will recognize that each codon in a nucleic acid (except AUG, which is ordinarily the only codon for methionine) can be modified by standard techniques to encode a functionally identical polypeptide. Accordingly, each silent variation of a nucleic acid which encodes a polypeptide is implicit in any described sequence. The invention provides each and every possible variation of nucleic acid sequence encoding a polypeptide of the invention that could be made by selecting combinations based on possible codon choices. These combinations are made in accordance with the standard triplet genetic code as applied to the nucleic acid sequence encoding a chitinase polypeptide of the invention. All such variations of every nucleic acid herein are specifically provided and described by consideration of the sequence in combination with the genetic code.

Polypeptides of the Invention

The present invention provides polypeptides that have a variety of uses. For example, the present invention provides polypeptides encoded by the open reading frames of SSLP039 (SEQ ID NO: 7) and SSLP090 (SEQ ID NO: 9). In addition, the invention also provides portions (e.g., unique subsequences) of the amino acid sequences of SEQ ID NOS: 7 and 9, polypeptides comprising the amino acid sequences of SEQ ID NOS: 7 and 9, and polypeptides comprising amino acid sequences that are homologous to SEQ ID NOS: 7 and 9. In some embodiments, the polypeptides of the invention have chitinase biological activity.

In one aspect, polypeptides provided by the invention find use, for example, as antigenic material for raising antibodies specific for the polypeptide. These antibodies find numerous uses, for example but not limited to, plant screening for the presence of the polypeptide in the selection of resistant plants, for use in the expression cloning of a cDNA or genomic fragment that encodes the full length gene from which EST SSLP039 or SSLP090 are derived, for the analysis of transgenic plants that expresses the SSLP039 chitinase gene, as well as in research.

The size and nature of the polypeptides that are used as antigenic material to produce antibodies is not particularly limited. For example, the antigenic material is not limited solely to the 176 amino acid polypeptide sequence provided in SEQ ID NO: 7 or the 86 amino acid polypeptide sequence provided in SEQ ID NO: 9. One of skill in the art recognizes that smaller portions, most preferably unique subsequences, of the polypeptides are preferably used as antigenic material. One of skill in the art will also recognize that various subsequences can be more or less desirable based on their amino acid content in view of the known antigenic properties of certain amino acids. Such information is widely known, and is available in various sources. The lower limit of a useful subsequence for antibody production is not limited, but has the provision that the subsequence results in the generation of polypeptide-specific antibodies from the animal host.

In one aspect, the invention provides polypeptides corresponding to (e.g., comprising) the SSLP039 EST, and most preferably, polypeptides having chitinase activity. As taught herein, full-length polypeptides, or suitable fragments thereof, having chitinase activity can be identified and isolated using various techniques well known in the art. For example, the SSLP039 EST polynucleotide sequence (SEQ ID NO: 1), or a portion thereof, can be used as a probe to screen and clone a cDNA from a soybean cDNA or genomic library. Alternatively, antibodies specific for the SSLP039 polypeptide sequence (SEQ ID. NO: 7) can be used to screen a soybean cDNA expression library for cDNA clones that express a polypeptide immuno-reactive with an SSLP039-specific antibody. Methods for the assessment of chitinase activity are known in the art, e.g., using the protocol provided in EXAMPLE 10.

In one aspect in accordance with the present invention, novel polypeptides having chitinase activity, homologues thereof, fragments (e.g., unique subsequences) thereof, related fusion proteins, or functional equivalents thereof, as well as the polynucleotides that encode them, find use in the construction of transgene expression constructs and transgenic plants that expresses the recombinant chitinase polypeptide, and provide the plant with resistance to various pathogens.

Due to the well known inherent degeneracy of the genetic code and permissiveness of conservative amino acid substitutions, other nucleic acid sequences and substantially similar or functionally equivalent polypeptides also find use in chitinase-encoding transgenes, and are also within the scope of the invention.

Modified Coding Sequences:

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang S P et al. (1991) *Gene* 105:61-72). Codons can be substituted to reflect the preferred codon usage of the host, a process called "codon optimization" or "controlling for species codon bias."

Optimized coding sequence containing codons preferred by a particular prokaryotic or eukaryotic host (see also, Murray, E. et al. (1989) *Nuc. Acids Res.* 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA respectively. The preferred stop codon for monocotyledonous plants is UGA, whereas insects and *E. coli* prefer to use UAA as the stop codon (Dalphin M E et al. (1996) Nuc. Acids Res. 24: 216-218).

The polynucleotide sequences of the present invention can be engineered in order to alter a chitinase coding sequence for a variety of reasons, including but not limited to, alterations which modify the cloning, processing and/or expression of the gene product. For example, alterations may be introduced using techniques which are well known in the art, e.g., site-directed mutagenesis, to insert new restriction sites, to alter glycosylation patterns, to change codon preference, to introduce splice sites, etc.

Vectors, Promoters and Expression Systems,

The present invention also includes recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), and the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts which describe molecular biological techniques useful herein, including the use of vectors, promoters and many other relevant topics, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., ("Ausubel")). Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

A vector containing an appropriate DNA sequence as described above, as well as an appropriate promoter or control sequence, may be employed to transform an appropriate host to permit the host to express the protein. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 or Bowes melanoma; plant cells, etc. It is understood that not all cells or cell lines need to be capable of producing fully functional chitinase polypeptides; for example, antigenic fragments of a chitinase polypeptide can be produced in a bacterial or other expression system. The invention is not limited by the host cells employed.

In bacterial systems, a number of expression vectors may be selected depending upon the use intended for the chitinase polypeptide. For example, when large quantities of chitinase polypeptide or fragments thereof are needed for the induction of antibodies, vectors which direct high level expression of fusion proteins that are readily purified may be desirable. Such vectors include, but are not limited to, multifunctional *E. coli* cloning and expression vectors such as BLUESCRIPT (Stratagene), in which the interferon homologue coding sequence may be ligated into the vector in-frame with sequences for the amino-terminal Met and the subsequent 7 residues of beta-galactosidase so that a hybrid protein is produced; pIN vectors (Van Heeke & Schuster (1989) *J Biol Chem* 264:5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the interferon homologue proteins of the invention. For reviews, see Ausubel et al. (supra) and Grant et al. (1987; *Methods in Enzymology* 153:516-544).

Secretion/Localization Sequences

Polynucleotides of the invention can also be fused, for example, in-frame to nucleic acids encoding a secretion/localization sequence, to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

Fusion Polypeptide Sequences

A variety of protocols and reagents are useful in the production of a chitinase polypeptide and related polypeptides. In some embodiments, the polypeptide is produced as a fusion protein, where the resulting polypeptide is an in-frame fusion between a chitinase coding sequence and at least one other coding sequence, and typically produced from transcription and translation of an engineered nucleic acid. A variety of fusion sequences are used for various purposes, for example but not limited to fusion tags that have highly specific antibodies, allowing the immunoprecipitation or visualization of the tagged polypeptide (alternatively called epitope tags), tags that permit the rapid purification of the tagged amino acid sequence, and fusion sequences that carry a biological (e.g., enzymatic or fluorescence) activity.

Common fusion tags include, but are not limited to, glutathione-S-transferase (GST) tag that binds glutathione, c-myc tag, metal chelating peptides such as histidine-tryptophan modules that allow purification on immobilized metals and 6-histidine (6×-His Tag), FLAG tag, green fluorescent protein (GFP), maltose binding protein (MBP), influenza A virus haemagglutinin (HA), β-galactosidase, GAL4, and thioredoxin-tag. The inclusion of a protease-cleavable polypeptide linker sequence between the tag and the chitinase sequence is also useful to facilitate purification.

Polypeptide Production and Recovery

In some embodiments, the polypeptide is synthetic, and is produced in a non-biological system. In some embodiments, the polypeptide is produced enzymatically in a biological system. In these biological systems, the polypeptide is typically a recombinant polypeptide. The recombinant polypeptide can be produced in any suitable host cell type (e.g., plant cells, bacterial cells or mammalian cells), typically using a species or cell-type specific overexpression system. The cultivation of the transformed, transfected or infected host cells of the invention is carried out in a medium under conditions most appropriate for the growth of that particular host cell. These media formulations and culture conditions are well known to one of skill in the art.

In a biological production system, following transduction of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

As noted, many references are available for the culture and production of many cells, including cells of bacterial, plant, animal and archebacterial origin. See e.g., Sambrook, Ausubel, and Berger (all supra), as well as Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelli, et al., (1989) *In vitro Cell Dev. Biol.* 25:1016-1024. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and *Plant Molecular Biolgy* (1993) R. R. D. Croy, Ed. Bios Scientific Publishers, Oxford, U.K. ISBN 0 12 198370 6. Cell culture media in general are set forth in Atlas and Parks (eds) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc (St Louis, Mo.) ("Sigma-LSRCCC") and, e.g., the *Plant Culture Catalogue* and supplement (1997) also from Sigma-Aldrich, Inc (St Louis, Mo.) ("Sigma-PCCS").

In other embodiments, the polypeptide is purified or enriched by any suitable method (for example, including but not limited to, phosphocellulose chromatography, hydroxylapatite chromatography, lectin chromatography, hydrophobic interaction chromatography, ammonium sulfate or ethanol precipitation, acid extraction, affinity chromatography (e.g., using any of the tagging systems noted above such as GST/gutathione tag purification or 6×His/nickel purification), immunoaffinity chromatography, size exclusion chromatography, anion or cation exchange chromoatography). Indeed, it is not intended that the present invention be limited to any particular polypeptide purification protocol. It is contemplated that any protocol that will produce a substantially purified polypeptide will find use with the present invention. A variety of polypeptide purification methods are known in the art, and are found in numerous sources. See, e.g., Ausubel et al. (eds.), Current Protocols in Molecular Biology, Vol. 1-4, John Wiley & Sons, Inc., New York [1994].

Protein refolding steps can be used, as desired, in completing configuration of the mature protein. Finally, high performance liquid chromatography (HPLC) can be employed in the final purification steps. In addition to the references noted supra, a variety of purification methods are well known in the art, including, e.g., those set forth in Sandana (1997) *Bioseparation of Proteins*, Academic Press, Inc.; and Bollag et al. (1996) *Protein Methods. $2^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice $3^{rd}$ Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ.

In Vitro Expression Systems

Cell-free transcription/translation systems can also be employed to produce polypeptides using DNAs or RNAs of the present invention. Several such systems are commercially available. A general guide to in vitro transcription and translation protocols is found in Tymms (1995) *In vitro Transcription and Translation Protocols: Methods in Molecular Biology* Volume 37, Garland Publishing, NY.

Homologous Nucleic Acids and Homologous Polypeptides

In addition, the SSLP039 and SSLP090 are useful for the identification of homologous nucleic acid sequences, e.g., with utility as markers. Such homologous markers are also a feature of the invention.

Homologous nucleic acids, e.g., homologous markers, can be identified by selective hybridization to a reference sequence. The reference sequence is typically a unique sequence, such as unique oligonucleotide primer sequences, ESTs, amplified fragments (e.g., corresponding to AFLP markers) and the like, derived from the marker loci SSLP039 or SSLP090, or its complement. Two single-stranded nucleic acids "hybridize" when they form a double-stranded duplex. The region of double-strandedness can include the full-length of one or both of the single-stranded nucleic acids, or all of one single stranded nucleic acid and a subsequence of the other single-stranded nucleic acid, or the region of double-strandedness can include a subsequence of each nucleic acid. Selective hybridization conditions distinguish between nucleic acids that are related, e.g,. share significant sequence identity with the reference sequence (or its complement) and those that associate with the reference sequence in a non-specific manner. Examples of selective hybridization conditions are those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Selective hybridization conditions may also be achieved with the addition of destabilizing agents such as formamide. Selectivity can be achieved by varying the stringency of the hybridization and/or wash conditions. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically a function of post-hybridization washes, with the critical factors being ionic strength and temperature of the final wash solution. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

The $T_m$ is the temperature (under defined ionic strength and pH) at which 50% of a complementary target sequence hybridizes to a perfectly matched probe. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/$L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C.

Using the equation, hybridization and wash compositions, and desired $T_m$, those of ordinary skill will understand that variations in the stringency of hybridization and/or wash solutions are described. If the desired degree of mismatching results in a $T_m$ of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120, or 240 minutes. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays" Elsevier, New York. General Texts which discuss considerations relevant to nucleic acid hybridization, the selection of probes, and buffer and incubation conditions, and the like, as well as numerous other topics of interest in the context of the present invention (e.g., cloning of nucleic acids which correspond to markers, sequencing of cloned markers, the use of promoters, vectors, etc.) can be found in Berger and Kimmel (1987) *Guide to Molecular Cloning Techniques, Methods in Enzymology* vol. 152, Academic Press, Inc., San Diego ("Berger"); Sambrook et al., (1989) *Molecular Cloning—A Laboratory Manual*, $2^{nd}$ ed. Vols. 1-3, Cold Spring Harbor Laboratory, Cold Spring Harbor ("Sambrook"); and Ausubel et al., (eds) *Current Protocols in Molecular Biology*, John Wiley and Sons, Inc., ("Ausubel").

In addition to hybridization methods described above, homologs of the markers of the invention can be identified in silico using any of a variety of sequence alignment and comparison protocols. For the purposes of the ensuing discussion, the following terms are used to describe the sequence relationships between a marker nucleotide sequence and a reference polynucleotide sequence:

A "reference sequence" is a defined sequence used as a basis for sequence comparison with a test sequence, e.g., a candidate marker homolog, of the present invention. A reference sequence may be a subsequence or the entirety of a specified sequence; for example, a segment of a full-length cDNA or gene sequence, or the complete cDNA or gene sequence.

As used herein, a "comparison window" is a contiguous and specified segment, (e.g., a subsequence) of a polynucleotide/polypeptide sequence to be compared to a reference sequence. The segment of the polynucleotide/polypeptide sequence in the comparison window can include one or more additions or deletions (e.g., gaps) with respect to the reference sequence, which (by definition) does not comprise addition(s) or deletion(s), for optimal alignment of the two sequences. An optimal alignment of two sequences yields the fewest number of unlike nucleotide/amino acid residues in a comparison window. Generally, the comparison window is at least 20 contiguous nucleotide/amino acid residues in length, and optionally can be 30, 40, 50, 100, or longer. Those of skill in the art understand that to avoid a falsely high similarity between two sequences, due to inclusion of gaps in the polynucleotide/polypeptide sequence, a gap penalty is typically assessed and is subtracted from the number of matches.

"Sequence identity" or "identity" in the context of two nucleic acid or polypeptide sequences refers to residues that are the same in both sequences when aligned for maximum correspondence over a specified comparison window.

"Percentage sequence identity" refers to the value determined by comparing two optimally aligned sequences over a comparison window. The percentage is calculated by determining the number of positions at which both sequences have the same nucleotide or amino acid residue, determining the number of matched positions, dividing the number of matched positions by the total number of positions in the comparison window, and multiplying the result by 100 to yield the percentage of sequence identity.

In some aspects, polynucleotides or polypeptides that share a high percentage of sequence identity with polynucleotides or polypeptides of the invention are also within the scope of the invention, and find use in the methods described herein. For example, polynucleotides that have a high percentage of sequence identity with SSLP039 (SEQ ID NO: 1) or SSLP090 (SEQ ID NO: 2) find use as molecular markers (e.g., probes or PCR primers); or alternatively, nucleic acid molecules that comprise a nucleotide sequence that displays a high percentage of sequence identity with SSLP039 (SEQ ID NO: 1) can encode a polypeptide having chitinase activity, which find use in the construction of disease-resistant transgenic plants. As described above, polynucleotides having at least 70% sequence identity with SSLP039 or SSLP090 find use with the invention. More preferably, polynucleotides with at least 75%, 80%, 85%, 90%, 95%, 97%, 98%, 99% or more sequence identity with SSLP039 or SSLP090 all find use with the invention, and are within the scope of the claimed invention.

When percentage of sequence similarity is used in reference to proteins it is recognized that residue positions which are not identical often differ by conservative amino acid substitutions, where one amino acid residue is substituted for other amino acid residue having similar chemical properties (e.g., aromatic side chains or positively charged side chains), and therefore do not substantially change the functional properties of the molecule.

Conservative amino acid substitutions can be characterized, for example, by substitutions within the following groups of amino acids:

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Where sequences differ by conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and one. The scoring of conservative substitutions is calculated, e.g., according to the algorithm of Meyers and Miller (1988) *Computer Applic. Biol. Sci.* 4:11-17, e.g., as implemented in the program PC/GENE (Intelligenetics, Mountain View, Calif., USA).

As used herein, "conservatively modified variations" or, simply, "conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

"Conservatively substituted variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group.

Finally, the addition of sequences which do not alter the encoded activity of a nucleic acid molecule, such as the addition of a non-functional sequence, is a conservative variation of the basic nucleic acid.

Methods of alignment of sequences for comparison are well-known in the art. Optimal alignment of sequences for comparison may be conducted by the local homology algorithm of Smith and Waterman (1981) *Adv. Appl. Math.* 2:482; by the homology alignment algorithm of Needleman and Wunsch (1970) *J. Mol. Biol.* 48:443; by the search for similarity method of Pearson and Lipman (1988) *Proc. Natl. Acad. Sci. USA* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp (1988) *Gene* 73:237-244; Higgins and Sharp (1989) *CABIOS* 5:151-153; Corpet et al. (1988) *Nucleic Acids Research* 16:10881-90; Huang et al. (1992) *Computer Applications in the Biosciences* 8:155-65, and Pearson et al. (1994) *Methods in Molecular Biology* 24:307-331.

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, e.g., *Current Protocols in Molecular Biology*, Chapter 19, Ausubel et al., Eds., (1995) Greene Publishing and Wiley-Interscience, New York; Altschul et al. (1990) *J. Mol. Biol.* 215:403-410; and, Altschul et al. (1997) *Nucleic Acids Res.* 25:3389-3402.

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see, e.g., Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-5877). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen (1993) *Comput. Chem.* 17:149-163) and XNU (Clayerie and States (1993) *Comput. Chem.* 17:191-201) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, e.g., Henikoff & Henikoff (1989) *Proc. Natl. Acad. Sci. USA* 89:10915).

Multiple alignment of the sequences can be performed using the CLUSTAL method of alignment (Higgins and Sharp (1989) *CABIOS.* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

The percentage sequence identity of a homologous marker to its reference marker (e.g., SSLP039 or SSLP090) is typically at least 80% and, rounded upwards to the nearest integer, can be expressed as an integer selected from the group of integers between 80 and 99. Thus, for example, the percentage sequence identity to a reference sequence can be at least 80%, 85%, 90%, 95%, 97%, or 99%. Sequence identity can be calculated using, for example, the BLAST, CLUSTALW, or GAP algorithms under default conditions.

Techniques for Marker Detection

The invention provides two EST molecular markers that are linked to known disease resistance loci. The markers find use in marker assisted selection for desired traits, and also have other uses. It is not intended that the invention be limited to any particular method for the detection of these two markers. Although the invention teaches a PCR-based method using radiolabelled primers to generate a detectable amplicon, as described in EXAMPLE 4, one of skill in the art will recognize that a variety of suitable equivalent protocols can be used to detect the markers. These alternative protocols are within the scope of the present invention.

In one embodiment, the presence or absence of a molecular marker is determined through nucleotide sequencing of the polymorphic marker region. Although this method is not as readily adapted to high throughput analysis as other methods taught herein, it is contemplated that nucleotide sequencing of the plant variable region to identify the presence or absence of a molecular marker is within the scope of the invention.

As described in EXAMPLES 3 and 4, the invention provides a method for detecting the EST molecular markers using plant genomic DNA as the analysis material. However, it is not intended that the invention be limited to the analysis of genomic material. Because the SSLP039 and SSLP090 markers are derived from expressed nucleotide sequences, it is contemplated that mRNA or cDNA can also serve as the source material for genetic analysis. For example, an RT-PCR method can be used to test for the presence of a marker sequence.

Markers corresponding to genetic polymorphisms between members of a population can be detected by numerous methods well-established in the art (e.g., PCR-based sequence specific amplification, restriction fragment length polymorphisms, isozyme markers, allele specific hybridization (ASH), amplified variable sequences of the plant genome, self-sustained sequence replication, simple sequence repeat (SSR), single nucleotide polymorphism (SNP), or amplified fragment length polymorphisms (AFLP).

The majority of genetic markers rely on one or more property of nucleic acids for their detection. For example, some techniques for detecting genetic markers utilize hybridization of a probe nucleic acid to nucleic acids corresponding to the genetic marker. Hybridization formats including but not limited to, solution phase, solid phase, mixed phase, or in situ hybridization assays. Markers which are restriction fragment length polymorphisms (RFLP) are detected by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals, and will often vary from line to line. Determining one or more restriction enzymes that produce informative fragments for each cross is a simple procedure, well known in the art. After separation by length in an appropriate matrix (e.g., agarose) and transfer to a membrane (e.g., nitrocellulose, nylon), the labeled probe is hybridized under conditions which result in equilibrium binding of the probe to the target followed by removal of excess probe by washing.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and calorimetric labels. Other labels include ligands which bind to antibodies labeled with fluorophores, chemiluminescent agents, and enzymes. Labeling markers is readily achieved such as by the use of labeled PCR primers to marker loci. A probe can also constitute radiolabelled PCR primers that are used to generate a radiolabelled amplicon.

In some embodiments, a nucleic acid probe is used to detect a nucleic acid that comprises the marker sequence (e.g., SSLP039 or SSLP090). Such probes can be used, for example, in positional cloning to isolate nucleotide sequences linked to the marker nucleotide sequence. It is not intended that the nucleic acid probes of the invention be limited to any particular size. For example, the probe sequences used to detect the SSLP039 or SSLP090 marker sequences can be of any suitable length that is longer or shorter than SEQ ID NOs: 1 or 2. In some embodiments, nucleic acid probe is at least 20 nucleotides in length, or alternatively, at least 50 nucleotides in length, or alternatively, at least 100 nucleotides in length, or alternatively, at least 200 nucleotides in length.

A hybridized probe is detected using, most typically by autoradiography or other similar detection technique (e.g., fluorography, liquid scintillation counter, etc.). Examples of specific hybridization protocols are widely available in the art, see, e.g., Berger, Sambrook, Ausubel, all supra.

Amplified variable sequences refer to amplified sequences of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

In vitro amplification techniques are well known in the art. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in Berger, Sambrook and Ausubel (all supra) as well as Mullis et al. (1987) U.S. Pat. No. 4,683,202; *PCR Protocols, A Guide to Methods and Applications* (Innis et al., eds.) Academic Press Inc., San Diego Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684, and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Oligonucleotides for use as primers, e.g., in amplification reactions and for use as nucleic acid sequence probes are typically synthesized chemically according to the solid phase phosphoramidite triester method described by Beaucage and Caruthers (1981) *Tetrahedron Lett.* 22:1859, or can simply be ordered commercially.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) Rnase H, and (3) a DNA-dependent RNA polymerase (Guatelli et al. (1990) *Proc Natl Acad Sci USA* 87:1874). By mimicking the retroviral strategy of RNA replication by means of cDNA intermediates, this reaction accumulates cDNA and RNA copies of the original target.

Amplified fragment length polymophisms (AFLP) can also be used as genetic markers (Vos et al. (1995) *Nucl Acids Res* 23:4407). The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping of plants (Becker et al. (1995) *Mol Gen Genet* 249:65; and Meksem et al. (1995) *Mol Gen Genet* 249:74).

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridizaiton. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are not excluded.

Alternatively, isozyme markers are employed as genetic markers. Isozymes are multiple forms of enzymes that differ from one another in their amino acid, and therefore their nucleic acid sequences. Some isozymes are multimeric enzymes contianing slightly different subunits. Other isozymes are either multimeric or monomeric but have been cleaved from the proenzyme at different sites in the amino acid seuqence. Isozymes can be characterized and analysed at the protein level, or alternatively, isozymes which differ at the nucleic acid level can be determined. In such cases any of the nucleic acid based methods described herein can be used to analyze isozyme markers.

Amplification Primers for Marker Detection

In some embodiments, the molecular markers of the invention are detected using a suitable PCR-based detection method, where the size or sequence of the PCR amplicon is indicative of the absence or presence of the marker. In these types of methods, PCR primers are directed to the conserved regions flanking the polymorphic marker region. As used in the art, PCR primers used to amplify a molecular marker are sometimes termed "PCR markers" or simply "markers."

It will be appreciated that the PCR primers used with the invention can be designed using any suitable method. It is not intended that the invention be limited to any particular primer or primer pair. For example, primers can be designed using any suitable software program, such as LASERGENE®, as described EXAMPLE 3.

In some embodiments, the primers of the invention are radiolabelled, or labelled by any suitable means (e.g., using a non-radioactive fluorescent tag), to allow for rapid visualization of the different size amplicons following an amplification reaction without any additional labelling step or visualization step. In some embodiments, the primers are not labelled, and the amplicons are visualized following their size resolution, e.g., following agarose gel electrophoresis. In some embodiments, ethidium bromide staining of the PCR amplicons following size resolution allows visualization of the different size amplicons.

It is not intended that the primers of the invention be limited to generating an amplicon of any particular size. For example, the primers used to amplify the SSLP039 or SSLP090 marker sequences are not limited to amplifying the entire SSLP039 (SEQ ID NO: 1) or SSLP090 (SEQ ID NO: 2) sequence. The primers can generate an amplicon of any suitable length that is longer or shorter than SEQ ID NOs: 1 or 2. In some embodiments, marker amplification produces an amplicon at least 20 nucleotides in length, or alternatively, at least 50 nucleotides in length, or alternatively, at least 100 nucleotides in length, or alternatively, at least 200 nucleotides in length.

Marker Assisted Selection and Breeding of Plants

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants that contain a desired genotype at one locus, or at several unlinked or linked loci (e.g., a haplotype), and that would be expected to transfer the desired genotype, along with a desired phenotype to their progeny. The present invention provides the means to identify plants, particularly soybean plant, that are resistant, or exhibit improved resistance to various pathogenic infections, for example, soybean mosaic virus (SMV), frogeye leaf spot and brown stem rot by identifying plants having a specified marker, e.g., markers SSLP039 or SSLP090, or homologous or linked markers. Similarly, by identifying plants lacking the desired marker, susceptible plants can be identified, and, e.g., eliminated from subsequent crosses.

In general, the application of MAS first requires the identification of a population of disease-resistant plants and genetic mapping of the resistance trait. Second, polymorphic loci in the vicinity of the mapped disease-resistance trait are chosen as potential resistance markers (typically, the marker closest to the disease-resistance locus is the preferred marker). Linkage analysis is then used to determine which polymorphic marker sequence demonstrates a statistical likelihood of co-segregation with the disease-resistance phenotype (the disease-resistance allele). Following the identification of marker for co-segregation with the disease-resistance allele, it is possible to use this marker for rapid, accurate screening of plant lines for the disease-resistance allele without the need to grow the plants through their life cycle and await phenotypic evaluations, and furthermore, permits genetic selection for the particular resistance gene allele despite the fact that the molecular identity of the resistance allele is still anonymous. Tissue samples can be taken, for example, from the first leaf of the plant and screened with the appropriate molecular marker, and within days it is determined which progeny will advance. Linked markers also remove the impact of environmental factors that can often influence phenotypic expression.

After a desired phenotype (e.g., resistance to soybean mosaic virus, frogeye leaf spot or brown stem rot) and a polymorphic chromosomal locus (e.g., an EST marker of the invention) are determined to cosegregate, the polymorphic locus can be used to select for alleles corresponding to the desired resistance phenotype—a process called marker-assisted selection (MAS). In brief, a nucleic acid corresponding to the marker nucleic acid is detected in a biological sample from a plant to be selected. This detection can take the form of hybridization of a probe nucleic acid to a marker, e.g., using allele-specific hybridization, Southern analysis, northern analysis, in situ hybridization, hybridization of primers followed by PCR amplification of a region of the marker or the like. A variety of procedures for detecting markers are described herein, e.g., in the section entitled "*TECHNIQUES FOR MARKER DETECTION.*" After the presence (or absence) of a particular marker in the biological sample is verified, the plant is selected, e.g., used to make progeny plants by selective breeding.

Soybean plant breeders need to combine disease resistance loci with genes for high yield and other desirable traits to develop improved soybean varieties. Disease screening for large numbers of samples can be expensive, time consuming, and unreliable. Use of the polymorphic markers described herein, when genetically-linked to disease resistance loci, are an effective method for selecting resistant varieties in breeding programs. For example, one advantage of marker-assisted selection over field evaluations for disease resistance is that MAS can be done at any time of year regardless of the growing season. Moreover, environmental effects are irrelevant to marker-assisted selection.

When a population is segregating for multiple loci affecting one or multiple traits, e.g., multiple loci involved in resistance to a single disease, or multiple loci each involved in resistance to different diseases, the efficiency of MAS compared to phenotypic screening becomes even greater because all the loci can be processed in the lab together from a single sample of DNA. In the present instance, the SSLP039 and SSLP090 markers can be assayed simultaneously or sequentially in a single sample or population of samples.

Another use of MAS in plant breeding is to assist the recovery of the recurrent parent genotype by backcross breeding. Backcross breeding is the process of crossing a progeny back to one of its parents. Backcrossing is usually done for the purpose of introgressing one or a few loci from a donor parent into an otherwise desirable genetic background from the recurrent parent. The more cycles of backcrossing that is done, the greater the genetic contribution of the recurrent parent to the resulting variety. This is often necessary, because resistant plants may be otherwise undesirable, e.g., due to low yield, low fecundity, or the like. In contrast, strains which are the result of intensive breeding programs may have excellent yield, fecundity or the like, merely being deficient in one desired trait such as resistance to a particular pathogen (e.g., soybean mosaic virus).

The presence and/or absence of a particular genetic marker, e.g., SSLP039 or SSLP090, or a homolog thereof, in the genome of a plant exhibiting a preferred phenotypic trait is made by any method listed above. If the nucleic acids from the plant are positive for a desired genetic marker, the plant can be self fertilized to create a true breeding line with the same genotype, or it can be crossed with a plant with the same marker or with other desired characteristics to create a sexually crossed hybrid generation.

Positional Cloning

The molecular markers of the present invention, e.g., SSLP039 and SSLP090, and nucleic acids homologous thereto, can be used, as indicated previously, to identify linked loci, which can be cloned by well established procedures, e.g., as described in detail in Ausubel, Berger and Sambrook, supra. Similarly, the SSLP markers, as well as any additionally identified linked nucleic acids, can be used to physically isolate, e.g., by cloning, nucleic acids associated with the markers that contribute to disease resistance.

These resistance nucleic acids are first identified by their genetic linkage to markers of the present invention. Isolation of the nucleic acid of interest is achieved by any number of methods as discussed in detail in such references as Ausubel, Berger and Sambrook, supra, and Clark, Ed. (1997) *Plant Molecular Biology: A Laboratory Manual* Springer-Verlag, Berlin.

For example, "positional gene cloning" uses the proximity of a genetic marker to physically define an isolated chromosomal fragment containing a resistance gene allele nucleic acid. The isolated chromosomal fragment can be produced by such well known methods as digesting chromosomal DNA with one or more restriction enzymes, or by amplifying a chromosomal region in a polymerase chain reaction (PCR), or any suitable alternative amplification reaction. The digested or amplified fragment is typically ligated into a vector suitable for replication, and, e.g., expression, of the inserted fragment. Markers that are adjacent to an open reading frame (ORF) associated with a phenotypic trait can hybridize to a DNA clone, thereby identifying a clone on which an ORF (or a fragment of an ORF) is located. If the marker is more distant, a fragment containing the open reading frame is identified by successive rounds of screening and isolation of clones which together comprise a contiguous sequence of DNA, a process termed "chromosome walking", resulting in a "contig" or "contig map." Protocols sufficient to guide one of skill through the isolation of clones associated with linked markers are found in, e.g. Berger, Sambrook and Ausubel, all supra.

Generation of Transgenic Cells and Plants

The present invention also relates to host cells and organisms which are transformed with nucleic acids corresponding to disease-resistance genes identified according to the invention. For example, such nucleic acids include chromosome intervals (e.g., genomic fragments), ORFs and/or cDNAs. Additionally, the invention provides for the production of polypeptides that provide disease-resistance by recombinant techniques. Host cells are genetically engineered (e.g., transduced, transfected or transformed) with the vectors of this invention (e.g., vectors which comprise an ORF derived from or related to the EST sequences) which are, for example, a cloning vector, a shuttle vector or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. The vectors are also introduced into plant tissues, cultured plant cells or plant protoplasts by a variety of standard methods known in the art, including but not limited to electroporation (From et al. (1985) *Proc. Natl. Acad. Sci. USA* 82;5824), infection by viral vectors such as cauliflower mosaic virus (CaMV) (Hohn et al. (1982) *Molecular Biology of Plant Tumors* (Academic Press, New York, pp. 549-560; Howell U.S. Pat. No. 4,407,956), high velocity ballistic penetration by small particles with the nucleic acid either within the matrix of small beads or particles, or on the surface (Klein et al. (1987) *Nature* 327;70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233;496; Fraley et al. (1983) *Proc. Natl. Acad. Sci. USA* 80; 4803). The method of introducing a nucleic acid of the present invention into a host cell is not critical to the instant invention, and it is not intended that the invention be limited to any particular method for introducing exogenous genetic material into a host cell. Thus, any suitable method, e.g., including but not limited to the methods provided herein, which provides for effective introduction of a nucleic acid into a cell or protoplast can be employed and finds use with the invention.

The engineered host cells can be cultured in conventional nutrient media modified as appropriate for such activities as, for example, activating promoters or selecting transformants. These cells can optionally be cultured into transgenic plants. Plant regeneration from cultured protoplasts is described in Evans et al. (1983) "Protoplast Isolation and Culture," *Handbook of Plant Cell Cultures* 1, 124-176 (MacMillan Publishing Co., New York; Davey (1983) "Recent Developments in the Culture and Regeneration of Plant Protoplasts," *Protoplasts*, pp. 12-29, (Birkhauser, Basel); Dale (1983) "Protoplast Culture and Plant Regeneration of Cereals and Other Recalcitrant Crops," *Protoplasts* pp. 31-41, (Birkhauser, Basel); Binding (1985) "Regeneration of Plants," *Plant Protoplasts*, pp. 21-73, (CRC Press, Boca Raton, Fla.).

The present invention also relates to the production of transgenic organisms, which may be bacteria, yeast, fungi, animals or plants, transduced with the nucleic acids of the invention, e.g., the cloned genes corresponding to the SSLP039 or SSLP090 EST's. A thorough discussion of techniques relevant to bacteria, unicellular eukaryotes and cell culture may be found in references enumerated above and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith (1979) *Gene* 8:81; Roberts et al. (1987) *Nature* 328: 731; Schneider et al. (1995) *Protein Expr. Purif.* 6435:10; Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA*, Second Edition, Scientific American Books, NY.

Transforming Nucleic Acids into Plants.

Embodiments of the present invention pertain to the production of transgenic plants comprising the cloned nucleic acids, e.g., isolated ORFs and cDNAs related to EST sequences SSLP039 and SSLP090. Techniques for transforming plant cells with nucleic acids are widely available and can be readily adapted to the invention. In addition to Berger, Ausubel and Sambrook, useful general references for plant cell cloning, culture and regeneration include Jones (ed) (1995) *Plant Gene Transfer and Expression Protocols— Methods in Molecular Biology, Volume* 49 Humana Press Towata N.J.; Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of cell culture media are described in Atlas and Parks (eds) *The Handbook of Microbiological Media* (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS). Additional details regarding plant cell culture are found in Croy, (ed.) (1993) *Plant Molecular Biology*, Bios Scientific Publishers, Oxford, U.K.

The nucleic acid constructs of the invention, e.g., plasmids, cosmids, artificial chromosomes, DNA and RNA polynucleotides, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acids of the present invention can be introduced into plants according to any of a variety of techniques known in the art. Techniques for transforming a wide variety of higher plant species are also well known and described in widely available technical, scientific, and patent literature. See, for example, Weising et al. (1988) *Ann. Rev. Genet.* 22:421-477.

The DNA constructs of the invention, for example plasmids, phagemids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting plant, e.g., cells, embryos, callus and protoplasts, are known in the art and well described in the scientific and patent literature. For example, a number of methods are described in Jones (ed) (1995) *Plant Gene Transfer and Expression Protocols—Methods in Molecular Biology, Volume* 49 Humana Press, Towata, N.J., as well as in the other references noted herein and available in the literature.

For example, the introduction of DNA constructs using polyethylene glycol precipitation is described in Paszkowski, et al., *EMBO J.* 3:2717 (1984). Electroporation techniques are described in Fromm, et al., *Proc. Natl. Acad. Sci. USA* 82:5824 (1985). Ballistic transformation techniques are described in Klein, et al., *Nature* 327:70-73 (1987). Additional details are found in Jones (1995) and Gamborg and Phillips (1995), supra, and in U.S. Pat. No. 5,990,387.

Alternatively, and in some cases preferably, *Agrobacterium* mediated transformation is employed to generate transgenic plants. *Agrobacterium*-mediated transformation techniques, including disarming and use of binary vectors, are also well described in the scientific literature. See, for example, Horsch, et al. (1984) *Science* 233:496; and Fraley et al. (1984) *Proc. Nat'l. Acad. Sci. USA* 80:4803 and recently reviewed in Hansen and Chilton (1998) *Current Topics in Microbiology* 240:22 and Das (1998) *Subcellular Biochemistry* 29: *Plant Microbe Interactions*, pp 343-363.

The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S.

Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller (1987) In: *Genetic Engineering*, vol. 6, P W J Rigby, Ed., London, Academic Press; and Lichtenstein; C. P., and Draper (1985) In: *DNA Cloning*, Vol. 1, D. M. Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) *Plant Cell Physiol.* 25:1353), (3) the vortexing method (see, e.g., Kindle (1990) *Proc. Natl. Acad. Sci.*, (*USA*) 87:1228.

DNA can also be introduced into plants by direct DNA transfer into pollen as described by Zhou et al. (1983) *Methods in Enzymology*, 101:433; D. Hess (1987) *Intern Rev. Cytol.* 107:367; Luo et al. (1988) *Plant Mol. Biol. Reporter* 6:165. Expression of polypeptide coding genes can be obtained by injection of the DNA into reproductive organs of a plant as described by Pena et al. (1987) *Nature* 325:274. DNA can also be injected directly into the cells of immature embryos and the desiccated embryos rehydrated as described by Neuhaus et al. (1987) *Theor. Appl. Genet.* 75:30; and Benbrook et al. (1986) in *Proceedings Bio Expo* Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Generation of Transgenic Plants

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al. (1983) *Protoplasts Isolation and Culture, Handbook of Plant Cell Culture* pp. 124-176, Macmillian Publishing Company, New York; and Binding (1985) *Regeneration of Plants, Plant Protoplasts* pp. 21-73, CRC Press, Boca Raton. Regeneration can also be obtained from plant callus, explants, somatic embryos (Dandekar et al. (1989) *J. Tissue Cult. Meth.* 12:145; McGranahan, et al. (1990) *Plant Cell Rep.* 8:512) organs, or parts thereof. Such regeneration techniques are described generally in Klee et al. (1987)., *Ann. Rev. of Plant Phys.* 38:467-486. Additional details are found in Payne (1992) and Jones (1995), both supra, and Weissbach and Weissbach, eds. (1988) *Methods for Plant Molecular Biology* Academic Press, Inc., San Diego, Calif. This regeneration and growth process includes the steps of selection of transformant cells and shoots, rooting the transformant shoots and growth of the plantlets in soil. These methods are adapted to the invention to produce transgenic plants bearing QTLs and other genes isolated according to the methods of the invention.

In addition, the regeneration of plants containing the polynucleotide of the present invention and introduced by *Agrobacterium* into cells of leaf explants can be achieved as described by Horsch et al. (1985) *Science* 227:1229-1231. In this procedure, transformants are grown in the presence of a selection agent and in a medium that induces the regeneration of shoots in the plant species being transformed as described by Fraley et al. (1983) *Proc. Natl. Acad. Sci.* (*U.S.A.*) 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

It is not intended that plant transformation and expression of polypeptides that provide disease resistance, as provided by the present invention, be limited to soybean species. Indeed, it is contemplated that the polypeptides that provide disease resistance in soybean can also provide disease resistance when transformed and expressed in other agronomically and horticulturally important species. Such species include primarily dicots, e.g., of the families: Leguminosae (including pea, beans, lentil, peanut, yam bean, cowpeas, velvet beans, soybean, clover, alfalfa, lupine, vetch, lotus, sweet clover, wisteria, and sweetpea); and, Compositae (the largest family of vascular plants, including at least 1,000 genera, including important commercial crops such as sunflower).

Additionally, preferred targets for modification with the nucleic acids of the invention, as well as those specified above, plants from the genera: *Allium, Apium, Arachis, Brassica, Capsicum, Cicer, Cucumis, Curcubita, Daucus, Fagopyrum, Glycine, Helianthus, Lactuca, Lens, Lycopersicon, Medicago, Pisum, Phaseolus, Solanum, Trifolium, Vigna*, and many others.

Common crop plants which are targets of the present invention include soybean, sunflower, canola, peas, beans, lentils, peanuts, yam beans, cowpeas, velvet beans, clover, alfalfa, lupine, vetch, sweet clover, sweetpea, field pea, fava bean, broccoli, brussel sprouts, cabbage, cauliflower, kale, kohlrabi, celery, lettuce, carrot, onion, pepper, potato, eggplant and tomato.

In construction of recombinant expression cassettes of the invention, which include, for example, helper plasmids comprising virulence functions, and plasmids or viruses comprising exogenous DNA sequences such as structural genes, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds or flowers.

Any of a number of promoters which direct transcription in plant cells can be suitable. The promoter can be either constitutive or inducible. In addition to the promoters noted above, promoters of bacterial origin that operate in plants include the octopine synthase promoter, the nopaline synthase promoter and other promoters derived from native Ti plasmids. See, Herrara-Estrella et al. (1983), *Nature,* 303: 209. Viral promoters include the 35S and 19S RNA promoters of cauliflower mosaic virus. See, Odell et al. (1985) *Nature,* 313:810. Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J.* 7:3315. Many other promoters are in current use and can be coupled to an exogenous DNA sequence to direct expression of the nucleic acid.

If expression of a polypeptide from a cDNA, including those cDNA species that were used to derive EST SSLP039 and SSLP090, is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes of the invention will typically include a nucleic acid subsequence, a marker gene which confers a selectable, or alternatively, a screenable, phenotype on plant cells. For example, the marker may encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos or Basta). See, e.g., Padgette et al. (1996) In: *Herbicide-Resistant Crops* (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See, Vasil (1996) In: *Herbicide-Resistant Crops* (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include RT-PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment of the invention is a transgenic plant that is homozygous for the added heterologous nucleic acid; e.g., a transgenic plant that contains two added nucleic acid sequences, one gene at the same locus on each chromosome of a chromosome pair. A homozygous transgenic plant can be obtained by sexually mating (self-fertilizing) a heterozygous transgenic plant that contains a single added heterologous nucleic acid, germinating some of the seed produced and analyzing the resulting plants produced for altered expression of a polynucleotide of the present invention relative to a control plant (e.g., a native, non-transgenic plant). Back-crossing to a parental plant and out-crossing with a non-transgenic plant are also contemplated.

Antibodies

The present invention provides novel polynucleotides derived from EST sequences, namely SSLP039 (SEQ ID NO: 1) and SSLP090 (SEQ ID NO: 2), as well as unique subsequences thereof. These polynucleotides are predicted to encode polypeptides shown in SEQ ID NO: 7 and SEQ ID NO: 9; respectively. The invention also provides polyclonal and monoclonal antibodies directed against these polypeptides.

These antibodies find numerous uses, for example but not limited to, plant screening for the presence of the polypeptide in the selection of resistant plants, for use in the expression cloning of a cDNA or genomic fragment that encodes the full length gene from which EST SSLP039 or SSLP090 are derived, for the analysis of transgenic plants that expresses the SSLP039 chitinase gene, as well as in research. The methods wherein such antibodies find use include but are not limited to immunoassays such as Western blotting, enzyme-linked immunosorbent assays (ELISAs), radioimmunoassays (RIAs), immunofluorescence assays (IFAs), immunoprecipitation, immunohistochemistry and immunoaffinity purification. All of these methods are well known in the art (See, e.g., Harlow and Lane (eds.), Antibodies: A Laboratory Manual, Cold Spring Harbor Laboratory Press [1988]; Ausubel et al. (eds.), Current Protocols in Molecular Biology, Vol. 1-4, John Wiley & Sons, Inc., New York [1994]).

As used herein, the term "antibody" (or "antibodies") refers to any immunoglobulin that binds specifically to an antigenic determinant, and specifically, binds to proteins identical or structurally related to the antigenic determinant which stimulated their production. Thus, antibodies are useful in methods to detect the antigen which stimulated their production. Monoclonal antibodies are derived from a single B lymphocyte clone and are generally homogeneous in structure and have polyepitopic antigen specificity. Polyclonal antibodies originate from many different clones of antibody-producing cells, and thus are heterogeneous in their structure and epitope specificity, but are generally enriched in antibodies which bind to same antigen. In some embodiments, purified monoclonal and/or polyclonal antibodies are used, while in other embodiments, crude preparations are used. For example, in some embodiments, polyclonal antibodies in crude antiserum are utilized. It is intended that the term "antibody" encompass any immunoglobulin (e.g., IgG, IgM, IgA, IgE, IgD, etc.) obtained from any source (e.g., humans, rodents, lagomorphs, non-human primates, caprines, bovines, equines, ovines, etc.).

As used herein, "antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 [1995]); single-chain antibody molecules; and multispecific antibodies formed from antibody fragments.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The "light chains" of antibodies (immunoglobulins) from any vertebrate species can be assigned to one of two clearly distinct types, called kappa and lambda, based on the amino acid sequences of their constant domains.

An "isolated" antibody is an antibody that has been enriched by the removal or partial removal of at least one contaminating component. Contaminant components are generally materials which could interfere with uses for the antibody, and may include, for example, enzymes, hormones, and other proteinaceous or nonproteinaceous solutes. In preferred embodiments, the antibody will be purified to greater than 95% by weight of antibody as determined by the Lowry method, and most preferably more than 99% by weight. Alternatively, an antibody will be purified to homogeneity or near homogeneity as assayed by SDS-PAGE under reducing or nonreducing conditions using Coomassie blue staining, or preferably, by silver staining. Isolated antibody includes the antibody in situ within recombinant cells since at least one component of the antibody's natural environment will not be present. Ordinarily, however, isolated antibody will be prepared using at least one enrichment step.

An antibody that "specifically binds" or is "specific for" a particular polypeptide or an epitope on a particular polypeptide is an antibody that binds to that particular polypeptide or epitope on a particular polypeptide without substantially binding to any other polypeptide or polypeptide epitope.

As used herein, the term "antigen" is used in reference to any substance that is capable of being recognized by an antibody. It is intended that this term encompass any antigen and "immunogen" (e.g., a substance which induces the formation of antibodies). Thus, in an immunogenic reaction, antibodies are produced in response to the presence of an antigen or portion of an antigen. The terms "antigen" and "immunogen" are used to refer to an individual macromolecule or to a homogeneous or heterogeneous population of antigenic macromolecules. It is intended that the terms antigen and immunogen encompass protein molecules or portions of protein molecules, which contain one or more epitopes. In many cases, antigens are also immunogens, thus the term "antigen" is often used interchangeably with the term "immunogen." An immunogenic substance can be used as an antigen in an assay to detect the presence of appropriate antibodies in the serum of an immunized animal.

The terms "antigenic determinant" and "epitope" as used herein refer to that portion of an antigen that makes contact with a particular antibody variable region. When a protein or fragment (or portion) of a protein is used to immunize a host animal, numerous regions of the protein may induce the production of antibodies which bind specifically to a given region or three-dimensional structure on the protein (these regions or structures are referred to as antigenic determinants). In some embodiments, an antigenic determinant (e.g., a fragment of an antigen) competes with the intact antigen (e.g., the "immunogen" used to elicit the immune response) for binding to an antibody.

The terms "specific binding" and "specifically binding" when used in reference to the interaction between an antibody and an antigen describe an interaction that is dependent upon the presence of a particular structure (e.g., the antigenic determinant or epitope) on the antigen. In other words, the antibody recognizes and binds to a protein structure unique to the antigen, rather than binding to all proteins in general (e.g., non-specific binding).

It is not intended that the present invention be limited to any particular method for antibody production. Numerous methods for the production and purification of antibodies are well known in the art, and can be found in various sources (See e.g., Sambrook et al. (eds.), Molecular Cloning, Cold Spring Harbor Laboratory Press [1989]; Harlow and Lane (eds.), Antibodies: A Laboratory Manual, Cold Spring Harbor Laboratory Press [1988]; Ausubel et al. (eds.), Current Protocols in Molecular Biology, Ch. 11, John Wiley & Sons, Inc., New York [1994]). Furthermore, it is not intended that the present invention be limited to any particular SSLP039 or SSLP090 polypeptide antigen or epitope, nor any particular method for the production of SSLP039 or SSLP090 polypeptide antigen. As skilled artisans know, numerous protocols for the production and purification of polypeptides (biologically produced or synthetically produced) suitable for use as antigens are available.

A variety of protocols and reagents are useful in the production of substantially purified SSLP039 or SSLP090 polypeptide, for example but not limited to, use as an antigen. In some embodiments of the present invention, the SSLP039 or SSLP090 antigen produced involves any suitable portion of the polypeptide. In other embodiments, a polypeptide can be produced with or without a fusion protein tag (e.g., GST, HA or FLAG), while in still further embodiments, the polypeptide is synthetic, recombinant or native. In additional embodiments, recombinant polypeptide is produced in various cell types (e.g., bacterial cells, mammalian cells or plant cells), while in still other embodiments, various expression vectors are used to drive expression of polypeptide within a cell. In further embodiments, polypeptide is purified by various methods (for example, including but not limited to, GST/gutathione tag purification). Indeed, it is not intended that the present invention be limited by any particular polypeptide purification protocol. It is contemplated that any protocol that will produce a substantially purified polypeptide will find use with the present invention. Such alternative protocols include the use of hemagglutinin (HA)-tagged fusion polypeptides, polyhistidine (6xHis)-tagged fusion polypeptides, thioredoxin-tagged fusion polypeptides, and polypeptides without any fused tag(s). In some embodiments, polypeptides suitable for use as antigenic material are produced by synthetic (non-enzymatic) chemistry.

Various protocols for recombinant polypeptide production also find use in the present invention. In some embodiments of the present invention, various host systems are used to produce starting material for polypeptide purification. Such systems include, for example, a wide range of bacterial and plant overexpression systems. The cultivation of the transformed, transfected or infected host cells of the invention is carried out in a medium under conditions most appropriate for the growth of that particular host cell. These media formulations and culture conditions are well known to one of skill in the art.

It is not intended that the present invention be limited to any particular method for the production of polyclonal antisera. One of skill in the art recognizes that there exist numerous alternative protocols and reagents that find use with the present invention to produce anti-SSLP039 or anti-SSLP090 antisera. For example, a full-length polypeptide, any portion thereof, either native, recombinant or synthetically produced, can be used to raise polyclonal antisera in any suitable animal (e.g., rabbit, rat, mouse, goat, etc.). In some embodiments, the antigen is mixed with an adjuvant (e.g., Freund's incomplete or complete adjuvant, or keyhole limpet hemocyanin [KLH]) prior to immunization of an animal. In addition, the dosage of the anitgen given to the animal can vary. In other embodiments, antigen is injected via intravenous, subcutaneous or intraperitoneal routes, and it is not intended that the interval of immunization, boosts or serum collection be limited to specific time points.

For preparation of monoclonal antibodies directed toward a chitinase polypeptide of the present invention, or variant or portion thereof, any technique that provides for the production of monoclonal antibody by continuous cell lines in culture can be used. These methods include but are not limited to the hybridoma technique originally developed by Kohler and Milstein (Kohler and Milstein, Nature 256:495-497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]). See also Harlow and Lane (eds.), Antibodies: A Laboratory Manual, Cold Spring Harbor Laboratory Press (1988); Harlow and Lane (eds.), Using Antibodies: A Laboratory Manual, Cold Spring Harbor Laboratory Press (1999); Coligan et al. (eds.), Current Protocols in Immunology, Vol. 1-4, John Wiley & Sons, Inc., New York (1991). It is not intended that the present invention be limited to the use of any particular protocol, as numerous protocols for generating antibody-producing cells are known, and find use in the present invention.

Following the production of polyclonal antisera or monoclonal antibodies, the antibodies can be purified using any suitable method, including but not limited to Protein A/Protein G affinity, ammonium sulfate salting out, ion exchange chromatography, gel filtration, affinity chromatography, or any of these methods in combination (See, e.g., Sambrook et al. (eds.), Molecular Cloning, Cold Spring Harbor Laboratory Press [1989]; Harlow and Lane (eds.), Antibodies: A Laboratory Manual, Cold Spring Harbor Laboratory Press [1988]; Ausubel et al. (eds.), Current Protocols in Molecular Biology, Ch. 11, John Wiley & Sons, Inc., New York [1994]; Harlow and Lane (eds.), Using Antibodies: A Laboratory Manual, Cold Spring Harbor Laboratory Press (1999); Coligan et al. (eds.), Current Protocols in Immunology, Vol. 1-4, John Wiley & Sons, Inc., New York [1991]). In view of numerous alternative protocols known in the art for the production and purification of polyclonal and monoclonal antibodies, it is not intended that the present invention be limited to any particular method for antibody purification.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Generation of Soybean ESTs

A total of 71 soybean EST libraries were constructed using mRNA isolated from a variety of plant tissues, including developing seed, leaves, roots, stem, immature flower, and plant embryo. Some of the plants that were used to construct the EST libraries were challenged with various pathogens such as SCN, *Sclerotinia* (white mold) and severe stunt virus. The libraries were constructed using well-established procedures.

The 71 EST libraries collectively yielded approximately 194,000 EST sequences. These 194,000 EST sequences were BLASTed against known "disease-related" plant sequences (including known disease-resistance and disease-response genes induced or upregulated in response to infection) to identify approximately 25,00 EST sequences of interest. The EST sequences were queried against the nucleotide database of the National Center of Biotechnology Information (NCBI) using the BLAST search tool.

These 25,000 ESTs were examined for sequence redundancy and other non-preferable characteristics, resulting in the identification of 1218 disease-related EST marker candidates. SSLP or SNP mapping strategies for the selected EST marker candidates were devised following close sequence analysis, and PCR primers for approximately 200 of the 1218 candidates were designed and produced. Approximately 50 of these candidates were mapped onto the soybean molecular linkage groups.

Based on their map locations and/or primary sequences, two of the mapped ESTs were of particular interest, namely, SSLP039 and SSLP090. These two ESTs were both isolated from a library generated from immature flower tissue isolated from a "Wye" soybean culitvar that was not challenged with any pathogen. The EST SSLP039 demonstrates strong homology to a known disease resistance gene.

SSLP039

The sequencing of this cDNA EST generated 532 nucleotides of sequence information, provided in SEQ ID NO: 1. One of the six possible reading frames of this nucleotide sequence yielded an open reading frame encoding a novel 176 amino acid polypeptide free of stop codons, provided in SEQ ID NO: 7. This was the only reading frame free of frequent stop codons. A single methionine appears in the sequence at the $10^{th}$ amino acid codon (M10). An open reading frame encoding nine amino acids also exists upstream of M10. The 167 amino acids downstream of M10 (SEQ ID NO: 8) are homologous, but not identical to, a known soybean ethylene-inducible acidic chitinase (Watanabe et al., Biosci. Biotechnol. Biochem., 63(2):251-256 [1999]; NCBI GenBank Accession Nos. AB006748, AB007126, AB007127; BAA77675 and BAA77676).

SSLP090

The sequencing of this cDNA EST generated 412 nucleotides of sequence information, provided in SEQ ID NO: 2. All six reading frames of this nucleotide sequence yielded polypeptide translations with frequent stop codons. The reading frame with the longest translation encoded a novel 86 amino acid polypeptide, with a single methionine at position 14 (M14). An open reading frame encoding 13 amino acids also exists upstream of M14.

Example 2

Marker Diversity Analysis

The polymorphic nature of the EST sequences SSLP039 and SSLP090 were tested in a marker diversity analysis (also called an allelic ladder). Twelve representative soybean materials consisting of wild and cultivated plant introductions from diverse origins were used in the analysis (see Table 1 below).

TABLE 1

Soybean Lines Used for Diversity Analysis

| Line Name | Species | Origin | Maturity | Type |
|---|---|---|---|---|
| Lee68* | *Glycine max* | Arkansas | VI | cultivar |
| Peking | *Glycine max* | China | IV | cultivar |
| Williams* | *Glycine max* | Illinois | III | cultivar |
| Wye | *Glycine max* | Maryland | IV | cultivar |
| V71-370* | *Glycine max* | Virginia | V | cultivar |
| PI96983* plant introduction line | *Glycine max* | Korea | V | cultivar |
| PI245331 plant introduction line | *Glycine soja* | Taiwan | X | wild |
| PI407162* plant introduction line | *Glycine soja* | Korea | IV | wild |
| PHP1 | *Glycine max* | | | cultivar |
| PHP2 | *Glycine max* | | | cultivar |
| PHP3 | *Glycine max* | | | cultivar |
| PHP4 | *Glycine max* | | | cultivar |

*Lines used to develop a mapping population.

The diverse strains included commercial cultivars, breeding lines and parental lines of mapping populations. The 12 lines were selected with the intention of providing a diverse gene pool for genetic screening with the EST's of this study. The sources covered origins spanning several states (Virginia, Illinois, Maryland and Arkansas) as well as Asia (China, Taiwan and Korea). Maturity classes ranging from III to VI and X were represented by the samples. Phenotypic traits between the twelve lines were noticeably diverse, including disease resistance responses. For example, line PI96983 is known to contain resistance genes for soybean mosaic virus, peanut mottle virus, and *Phytophthora*, while Lee68 is known to be susceptible to all three of these diseases.

Commercial cultivars and breeding lines were obtained from the soybean-breeding program at Virginia Tech. Dr. R. Nelson, United States Department of Agriculture, Agriculture Research Service (USDA-ARS), at the University of Illinois supplied the plant introductions. Four *Glycine max* lines supplied by DUPONT®-PIONEER Hi-Bred® (PHP lines) were also used in the diversity analysis. Other lines are known in the art, and descriptions can be found on the website for the Germplasm Resources Information Network (GRIN) maintained by the Department of Agriculture's Agricultural Research Service.

Example 3

SSLP EST Marker Primer Design

The nucleotide sequences of EST marker candidates SSLP039 and SSLP090 were queried against the public NCBI soybean EST database using the BLAST search tool. The search results were scanned for SSR and insertion/deletion mutations that may produce favorable polymorphism at that locus in different soybean genomes (lines).

The Primer Select feature of LASERGENE® Version 4.0.3 manufactured by DNASTAR® Inc. (Madison, Wis.) was used to design primers that amplify 150 to 300 base pair regions of the SSLP039 and SSLP090 sequences which were predicted to include potentially polymorphic regions. The forward and reverse primers used to amplify SSLP039 are provided in SEQ ID NOS: 3 and 4, respectively. The forward and reverse primers used to amplify SSLP090 are provided in SEQ ID NOS: 5 and 6, respectively. These primers used with the present invention are exemplary only, as other suitable primers are easily designed and generated.

Example 4

Soybean DNA Sample Collection for Marker Diversity Analysis

DNA samples from the various soybean lines in Table 1 were collected. To accomplish this, young leaves were collected and bulked from plants of each line to make DNA for the analysis. Soybean genomic DNA was extracted from powdered freeze-dried tissue with CTAB extraction buffer (50 mM Tris, 0.7 M NaCl, 10 mM EDTA, 1% hexadecyltrimethylammonium bromide, 0.1% 2-mercaptoethanol), adhering to the protocol described previously in Maroof et al. (*PNAS*, 81:8014-8018 [1984]).

Briefly, freeze-dried leaflet tissue (0.75 g, dry weight) was ground with a mechanical mill, dispersed in 15 mL of CTAB extraction buffer, and incubated at 65° C. for 60 minutes in a shaker bath. Ten mL of chloroform/octanol (24:1) were added. The solution was mixed by inversion and then centrifuged at 3200 rpm at 4° C. for 15 minutes. The aqueous phase was transferred to a new tube. Two third volumes of isopropanol was added and mixed by inversion. The precipitated pellet of DNA was hooked with a glass rod and transferred to a glass tube containing 20 mL 76% EtOH/10 mM $NH_4Ac$. After overnight washing in the EtOH solution, the DNA pellet was air dried and then dissolved in 10 mM $NH_4OAc$/0.25 mM EDTA. A fluorometer reading was taken for each DNA sample in order to measure the DNA concentration. Uncut DNA was run on 0.8% agarose gel to check its quality.

The SSLP screening procedure was essentially identical to microsatellite analysis as described by Maroof et al. (*PNAS*, 91:5466-5470 [1994]) and Yu et al. (*Phytopathology* 84:60-64 [1994]). Briefly, a 10 µL PCR reaction contained 50 ng of plant genomic DNA, 0.1 mM of each PCR primer, 10× reaction buffer, 3 mM $MgCl_2$, 200 mM each dATP, dGTP, dTTP, 5 mM dCTP, 1.0 U of AmpliTaq DNA polymerase (PERKIN-ELMER®/CETUS, Norwalk, Conn.), and 0.05 µCi [$\alpha$-$^{32}$P] dCTP. The reaction was denatured at 94° C. for 3 minutes, followed by 32 cycles at 94° C. for 30 seconds, 47° C. for 30 seconds, and 68° C. for 1 minute, with a final extension step at 68° C. for 7 minutes. PCR products were denatured at 94° C. for 8 minutes after loading buffer (98% deionized formamide, 10 mM EDTA (pH 8.0), 0.25% xylene cyanol FF, 0.25% bromophenol blue) was added. Five microliters of each sample was loaded on a polyacrylamide denaturing gel and separated at 1500-V constant power in 1×TBE (Tris-Borate-EDTA) running buffer, using a DNA sequencing unit (Model STS-45, IBI®, New-Haven, Conn.). Gels were immediately covered with plastic wrap and exposed to X-ray film.

Example 5

Marker SSLP Polymorphism and Statistical Analysis

The SSLP markers were evaluated as a whole based on their ability to detect at least one variant (a total of two alleles) in the set of representative soybean lines. Diversity level of each locus was evaluated using a genetic diversity index $(1-\Sigma p_i^2)$, where $p_i$ is the frequency of the $i^{th}$ allele, as described by Nei (*PNAS* 70:3321-3323 [1973]) and Yang et al. (*Mol. Gen. Genet.*, 245: 187-194 [1994]).

The diversity index is a statistical way to measure the potential usefulness of a marker. The index is expressed in a scale from a hypothetical zero to a hypothetical one, with zero being the least useful (a marker can not detect any polymorphism), and one being the hypothetically most useful (the ability to detect multiple polymorphisms). The diversity index will approach but will never reach the values of zero or one. The larger the diversity value indicates that more alleles are detectable. The number of plant lines assessed will also determine the diversity value range. Diversity index values don't necessarily have to have a value close to one to indicate a potentially useful marker.

Polymorphic alleles that differ in size will create allelic ladders when visualized according to the marker analysis method described in EXAMPLE 4. Each step of the ladder represents a different size band and can be used to differentiate genotypes.

Using the method described in EXAMPLE 4, a diversity analysis was done using the PCR markers specific for the SSLP039 and SSLP090 EST sequences. PCR amplicons specific for the SSLP039 marker were generated using the radio-labelled PCR primers of SEQ ID NOS: 3 and 4 and template DNA from each of the twelve soybean lines, loaded into separate lanes, and resolved on a polyacrylamide gel. The bands were then visualized with X-ray film. This analysis using the SSLP039 marker yielded an allelic ladder showing at least two different sized alleles among the 12 lines tested shown in Table 1. The two different size alleles detected were assigned the letters A or B.

Similarly, PCR amplicons specific for the SSLP090 marker were generated using the radiolabelled PCR primers of SEQ ID NOS: 5 and 6 and template DNA from each of the twelve soybean lines, loaded into separate lanes, and resolved on a polyacrylamide gel. The bands were then visualized with X-ray film. This analysis using the SSLP090 marker yielded an allelic ladder showing at least six different sized alleles among the 12 lines tested shown in Table 1. The different size alleles detected were assigned the letters A through F.

This allele polymorphism data is summarized in Table 2 below.

TABLE 2

Allele Variant Analysis and Diversity Index

| Soybean Line | EST | |
| --- | --- | --- |
| | SSLP039 | SSLP090 |
| Wye | A | D |
| Williams | B | A |
| PI96983 | A | A |
| Lee68 | B | B |
| PI407162 | A | B |
| V71-370 | B | C |
| PI245331 | B | E |
| Peking | A | D |
| PHP1 | B | A |
| PHP2 | B | A |
| PHP3 | A | F |
| PHP4 | B | A |
| Diversity Index | 0.486 | 0.750 |
| # of variants detected | 2 | 6 |

Example 6

Mapping Population

A total of 114 recombining inbred lines (RILs) were developed from the interspecific hybridization between an adapted, large-seeded (24 g/100 seeds), high sucrose (8.3%) *Glycine max* breeding line (V71-370), and a small seeded (1.8 g/100 seeds), low sucrose (1.6%) *Glycine soja* plant introduction (PI407162). It was assumed that the extensive phenotypic differences between the two lines is indicative of significant genetic variation between the lines, facilitating the marker analysis. These parental lines are known in the art, and are described in, for example, Maughan et al., "Molecular Marker Analysis of Seed-Weight: Genomic Locations, Gene Action and Evidence of Orthologous Evolution Among Three Legume Species," *Theor. Appl. Genet.*, 93:574-579 (1996); and Maughan et al., "Identification of Quantitative Trait Loci Controlling Sucrose Content in Soybean (*Glycine max*)," *Molecular Breeding* 6:105-111 (2000).

The RILs were developed using a modified single-seed descent method. Four seeds were chosen at random from each plant in each generation and bulked, starting with the F2 that was grown in the field at Eastern Virginia Agriculture Research and Extension Center, near Warsaw, Va. Lines were carried forward from the F3 to the F8 generation, allowing plants to self-pollinate in the greenhouse at Virginia Tech. A single seed was used in the generation F5 through F8 in the greenhouse. Bulked seed from each F8 plant was grown in the field in individual rows at Warsaw, Va., in 1998. Young leaves were then taken from each plant to be used for DNA extraction. These RILS were previously genotyped with a set of RFLPs and SSRs (Cicek, "Genetic analysis of quantitative trait loci associated with seed sucrose content using molecular markers in an interspecific Glycine cross," M.S. Thesis, Department of Crop and Soil and Environmental Sciences, Virginia Tech, Blacksburg, Va. [1997]).

Example 7

DNA Extraction from Soybean Mapping Population

DNA from each parent and RIL was isolated from the plant leaves according to the protocol described in EXAMPLE 4, and also as described in Maroof et al. (*PNAS,* 81:8014-8018 [1984]).

Example 8

Marker Analysis

The map locations of SSLP039 and SSLP090 were determined following establishment that the parental lines, V71-370 and PI407162 (used to develop the mapping population), carried different genotypes. Published SSR primers detecting polymorphism between the parents were selected, approximately 20 cM apart, to span each chromosomal linkage group. The SSLP markers were mapped in an F8 V71-370 X PI407162 recombining inbred line (RIL) population. The SSLP039 and SSLP090 markers were applied to the 114 RIL mapping population using PCR analysis. Where necessary, the PCR conditions were manipulated to improve the distinctness of amplification products. In general, increasing the number of cycles was sufficient to increase band intensity and resolution. For a given marker, individuals that inherited the allele of V71-370 were scored as A, and individuals that inherited the allele of PI407162 were scored as B. The inheritance pattern of each framework marker on linkage groups D1b and J was analyzed, in addition to the inheritance patterns of SSLP039 and SSLP090. FIGS. 1A through 1D provide a table showing the inherited marker allele analysis from approximately 114 recombinant inbred soybean lines (RIL) for eight framework markers on linkage group D1b, four framework markers on linkage group J, and the SSLP039 and SSLP090 EST markers. The analysis summarized in FIGS. 1A through 1D also incorporate three additional SSLP EST markers (SSLP048, SSLP108 and SSLP181) and one resistance gene analogue locus (RGA43). This data was used for recombination analysis in map construction as described in EXAMPLE 9.

Example 9

Map Construction

MAPMAKER Version 3.0 (Lincoln et al., *Proc. Nat. Acad. Sci. U.S.A* 84:2363-2367 [1987]) was used to group and order the genetic loci in the study. The published markers represented a skeletal map of each chromosome that was used to identify the positions of SSLP039 and SSLP090. Marker loci were grouped at LOD 3.0 (logarithm to the base 10 of likelihood odds ratio) with a maximum Haldane distance of 50 centiMorgans. Publicly available SSR markers were added to the representative linkage groups throughout the project in an effort to close all gaps.

Known soybean disease-resistance genetic loci were superimposed onto the skeletal framework map by associating markers reported to be linked to the disease resistance locus known in the published literature with known markers on the skeletal map. These disease resistance genes, and the markers used to place them on the genetic map them, are shown in Table 3 below. The specific linkage distances that were reported between the markers and the resistance genes are recorded in parenthesis and are in centimorgans (cM). In some cases, "bins" are created that represent regions of a linkage group, so that resistance genes and molecular markers from the same region can be grouped together. However, the precise locations of the genes and markers within a bin are not well defined.

SSLP markers, as described herein. The distance column under the framework marker indicates the estimated map distance between the framework marker and the EST marker. These numbers are zero, indicting that the EST markers and the framework markers colocalized (within the resolution of the skeletal framework genetic map). In other words, the SSLP039 marker maps to approximately the same location as the Satt244 framework marker on linkage group J. Similarly, the SSLP090 marker maps to approximately the same position as the Satt558 marker on linkage group D1b.

The reported disease-resistance marker column shows how the EST markers are associated with the disease resistance genes superimposed on the skeletal map. The reported marker column indicates the previously published resistance-marker that has been linked to the disease-resistance locus. In these two cases, the linked resistance marker also appears on our framework map. The first distance number given in the reported resistance-marker column is an estimated distance between the reported resistance marker and the framework marker. In the case of SSLP039 and SSLP090, this distance is zero because the framework marker and the published disease-resistance marker are the same marker. The second number given is an estimated distance between the EST marker and the resistance gene. As can be seen in the table, the presently identified novel SSLP039 marker maps to linkage group J approximately in same genetic position as the previously identified Satt244 marker, and the Satt244 marker has been previously mapped to approximately 1.1 cM from the Rcs3 disease resistance locus. Furthermore, from available

TABLE 3

Known Disease Resistance Genes

| Disease Resistance | Gene | Linkage Group | Reported Markers and Distance from Resistance Locus | Reference |
|---|---|---|---|---|
| Soybean Mosaic Virus (SMV) | Rsv4 | D1b | Satt542 (4.7 cM) Satt558 (7.8 cM) | Hayes et al., Crop Science 40: 1434-1437 [2000]; Hayes et al., Theor. Appl. Genet., 101: 789-795 [2000] |
| Frogeye Leaf Spot | Rcs3 | J | Satt244 (1.1 cM) | Yang et al., Plant Breeding 120: 73-78 [2001] |
| Brown Stem Rot | Rbs1 | J | Satt215 and Satt431 | Bachman et al., Crop Science 41: 527-535 [2001] |
| Brown Stem Rot | Rbs2 | J | Satt244 and Satt431 | Bachman et al., Crop Science 41: 527-535 [2001] |
| Brown Stem Rot | Rbs3 | J | Binned with Rbs1 and Rbs2 | Shoemaker et al., 2003. .Soybase class browser: Pathology. Iowa: Iowa State University, http://soybase.ncgr.org/cgi-bin/ace/generic/search/soybase |

The EST-derived markers SSLP039 and SSLP090 were integrated into the framework skeletal map, and their map locations relative to known disease resistance loci were examined, as shown in Table 4 below. The resistance genes indicated are those resistance loci that were superimposed on the skeletal framework map by their association with known framework markers. The framework markers indicated are those markers that were linked experimentally to the EST data, it is likely that the SSLP039 marker also maps within 10 cM of at least a subset of the Rbs cluster genes on linkage group J.

Similarly, the presently identified novel SSLP090 marker maps to linkage group D1b at approximately same genetic position as the previously identified Satt558 marker, and that Satt558 marker has been previously mapped to a location approximately 7.8 cM from the Rsv4 disease resistance locus.

TABLE 4

Association of EST markers with Disease Resistance Markers

| EST Marker | Linkage Group | Associated Resistance Gene | Framework Marker | | Reported Disease-Resistance Marker | |
|---|---|---|---|---|---|---|
| | | | Marker | Distance from EST Marker (cM) | Marker | Distance from EST Marker (cM) |
| SSLP039 | J | Rcs3, Rbs1, Rbs2 and Rbs3 | Satt244 | 0.0 | Satt244 | 0.0/1.1 |
| SSLP090 | D1b | Rsv4 | Satt558 | 0.0 | Satt558 | 0.0/7.8 |

Figure 3:
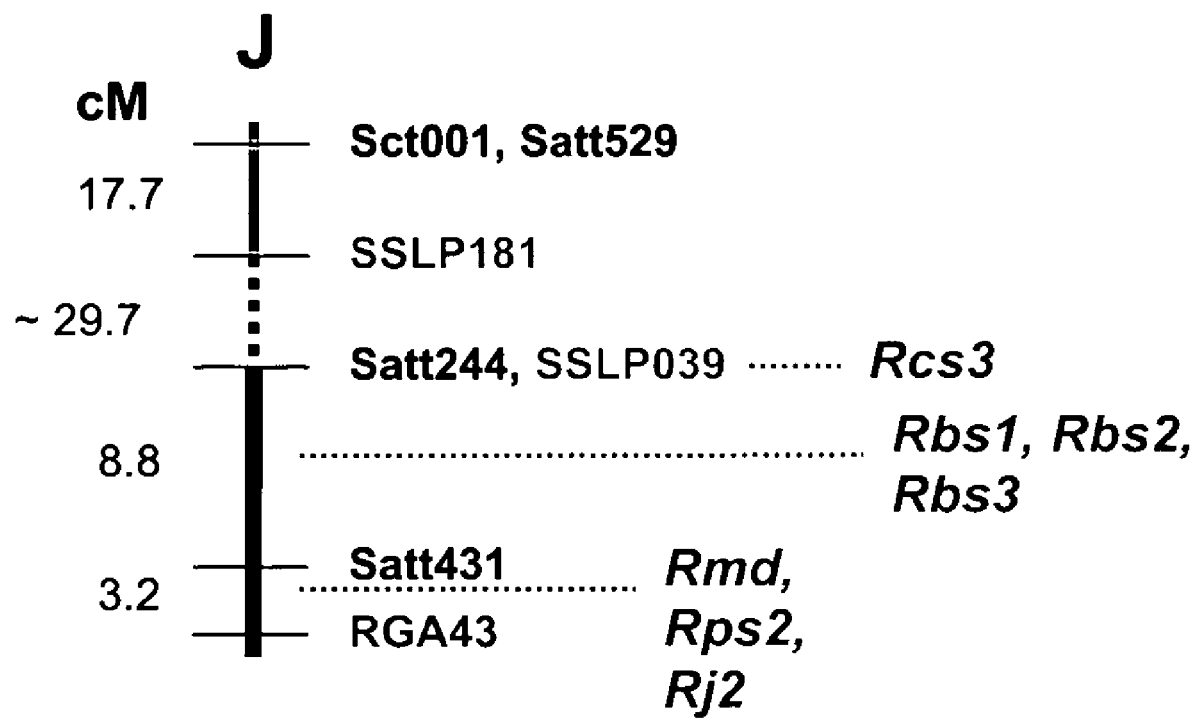
FIG. 3 provides a genetic linkage map for soybean linkage group J. EST markers SSLP181 and SSLP039 are indicated on the map.

The assembled maps of soybean linkage groups D1b and J are shown in FIGS. 2 and 3, respectively. In total, approximately 200 SSLP EST markers were mapped onto the soybean molecular linkage groups; only those EST markers that mapped to linkage groups D1b and J are indicated in FIGS. 2 and 3. FIG. 2 provides a genetic linkage map for soybean linkage group D1b, based on the mapping results of the framework markers (see Cregan et al., *Crop Sci.*, 39:1464-1490 [1999]) and the SSLP mapping results provided herein. The SSLP markers were mapped using recombinant lines (RILs) of F8 V71-370 X PI407162. Map distances are given in centimorgans (cM) to the left of each linkage group. The vertical lines represent the relative distance between adjacent markers. The wide solid black line represents genetic distances drawn to scale. The thinner grey lines represent genetic distances that are too large to draw to scale on this map. The hatched lines represent gaps in the genetic maps or ambiguous distance relationships. The mapped framework markers are indicated by Sat or Satt; SSLP048, SSLP090 and SSLP108 are SSLP EST markers placed on the map by the present work. Rsv4 indicates the map position of the previously identified soybean mosaic virus resistance gene locus.

FIG. 3 provides a genetic linkage map for soybean linkage group J. The mapped framework markers are indicated by Sct or Satt. SSLP181 and SSLP039 are SSLP EST markers placed on the map by the present work. Rcs3 indicates the map position of the frogeye leaf spot resistance gene; Rbs1, Rbs2 and Rbs3 indicate the map position of brown stem rot resistance gene 1, 2 and 3, respectively. RGA43 indicates the approximate map location of a resistance gene analogue gene locus. Also shown on the linkage group J map are the genetic loci for the powdery mildew resistance gene (Rmd), phytopthora resistance gene (Rps2) and nodulation resistance gene (Rj2). One mapped resistance gene analog (RGA43) is also shown on the map.

Example 10

Chitinase Activity Assay

Various methods are known in the art for the assay of chitinase activity. For example, an assay to measure chitinase activity is provided in Yeboah et al., Plant Mol. Bio., 36:407-415 [1998]. In this method, chitinase activity is assayed in a reaction mixture (550 µL) composed of 500 µL of 2% (w/v) ethylene glycol chitin (Seikagaku Kogyo Co., JAPAN), dissolved in 100 mM sodium acetate buffer (pH 5.2) and 50 µL of an enzyme test solution. After incubation of the mixture at 37° C. for 30 minutes, reducing sugars released by the enzyme action are determined by the Somogyi-Nelson method (Nelson, J. Biol. Chem., 153:375-380 [1944]).

One unit of chitinase activity was defined as that amount of activity that is required to yield a soluble reducing sugar equivalent to 1 µg of dextrose per minute per mL of reaction mixture. The specific activity is defined as enzyme activity units per mg of protein. Protein content can be determined by any suitable method, for example, the Bradford assay method.

Example 11

Summary of SEQ ID Listing

TABLE 5

| SEQ ID NO: | Description | Sequence |
|---|---|---|
| 1 | SSLP039 EST 532 nt | GCACGAGAGAGAATACACCAAAACCCAACATGAAAACCCTTAAC AAAGCCTCACTTATTTTATTCCCTCTCTTGTTCCTTTCCCTATT CAAGCATTCCCATGCTGCAGGAATCGCTGTCTACTGGGGCCAAA ACGGTGGAGAAGGCACCTTAGCAGAAGCTTGCAACACTAGAAAC TACCAATATGTGAACATAGCCTTCTTGTCCACTTTTGGCAACGG CCAAACTCCACAACTCAACCTTGCAGGTCATTGTGACCCCAACA ACAATGGCTGCACTGGGTTGAGCAGTGACATCAAAACTTGCCAA GACCTTGGCATCAAAGTGTTGCTCTCCCTTGGTGGTGGTGCTGG AAGCTACTCCCTCAGCTCAGCTGATGATGCCACTCAACTTGCAA ACTACCTCTGGCAGAATTTCCTTGGAGGTCAAACCGGATCAGGG CCATTAGGTAATGTTATATTGGATGGCATTGACTTTGACATTGA ATCTGGTGGGAGTGACCATTATGATGACCTAGCCAGGGCATTAA ATAG |

TABLE 5-continued

| SEQ ID NO: | Description | Sequence |
|---|---|---|
| 2 | SSLP090 EST 412 nt | GAAATTTCCAAGGACTAGTTCCCTTACTCATCTTTTGGAAATGG ATTACTTGGGTCCAATATCACATATATTATCTGATGCCACATAC AATTCAACCTTTGATTTTCAAATTAACACTGCCAATGGTGGAAT AGACCCGTTCGTAAAACCACAGCCGGTTGAAATCCCTTATGCAG CAGATTCAGGGAAGTACCAAGTGAAACAAAATAGCACCATCAAC CCCACCATATTTGTGAACCAAGTGTATTATCAAAGAGGATAATG CCAAAAAAATATTAAAAAAATGAAATTGGATTATTTGGACAT GACGATAAGCGTCACCAATTAAATAATCCTGAAGTTCTTTGTAA ATATATATATATATATATATATATATATATATATATATATATAT ATATATATATATAT |
| 3 | SSLP039 forward PCR primer | GCCTCACTTATTTTATTCCCTCTC |
| 4 | SSLP039 reverse PCR primer | GCCCAGTGCAGCCATTGTTGT |
| 5 | SSLP090 forward PCR primer | TTGGATTATTTGGACATGACGATA |
| 6 | SSLP090 reverse PCR primer | GGGGAGTGTTACTTAATGAATGGTA |
| 7 | SSLP039 translation (with 9 aa upstream of Met) 176 aa | TRENTPKPNMKTLNKASLILFPLLFLSLFKHSHAAGIAVYWGQN GGEGTLAEACNTRNYQYVNTAFLSTFGNGQTPQLNLAGHCDPNN NGCTGLSSDIKTCQDLGIKVLLSLGGGAGSYSLSSADDATQLAN YLWQNFLGGQTGSGPLGNVILDGIDFDIESGGSDHYDDLARALN |
| 8 | SSLP039 translation (without 9 aa upstream of Met) 167 aa | MKTLNKASLILFPLLFLSLFKHSHAAGIAVYWGQNGGEGTLAEA CNTRNYQYVNIAFLSTFGNGQTPQLNLAGHCDPNNNGCTGLSSD IKTCQDLGIKVLLSLGGGAGSYSLSSADDATQLANYLWQNFLGG QTGSGPLGNVTLDGTDFDTESGGSDHYDDLARALN |
| 9 | SSLP090 partial translation 86 aa | KFPRTSSLTHLLEMDYLGPISHTLSDATYNSTFDFQINTANGGI DPFVKPQPVEIPYAADSGKYQVKQNSTTNPTIFVNQVYYQRG |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for selecting a disease-resistant soybean plant, the method comprising:
   a) detecting a marker nucleic acid, wherein the marker nucleic acid maps ten centimorgans or less from a disease-resistance gene allele, wherein the marker comprises the polynucleotide sequence of SEQ ID NO: 1 (SSLP039), or a polynucleotide sequence that is completely complementary to SEQ ID NO: 1, and wherein the disease-resistance gene allele is selected from the group consisting of resistance alleles of frogeye leaf spot resistance gene (Rcs3), brown stem rot resistance gene 1 (Rbs1), brown stem rot resistance gene 2 (Rbs2) and brown stem rot resistance gene 3 (Rbs3); and,
   b) selecting a plant comprising the marker nucleic acid, thereby selecting a disease-resistant plant.

2. The method of claim 1, wherein the detecting comprises amplifying the marker nucleic acid or a portion of the marker nucleic acid and detecting the resulting amplified marker nucleic acid and wherein the amplifying produces a marker amplicon.

3. The method of claim 2, wherein the amplifying comprises performing a polymerase chain reaction (PCR) using one or more nucleic acid from the plant as a template in the PCR.

4. The method of claim 3, wherein the PCR comprises a primer pair having the nucleotide sequence of SEQ ID NOs: 3 and 4.

5. The method of claim 1, wherein the soybean plant is a progeny plant resulting from a plant cross between a first plant comprising the disease-resistance gene allele and a second plant that does not comprise the disease-resistance gene allele.

6. The method of claim 5, wherein the method further comprises introgressing the disease-resistance gene allele into offspring of the progeny soybean plant.

7. A method for selecting a disease-resistant soybean plant, the method comprising:
   a) detecting a marker nucleic acid, wherein the marker nucleic acid maps ten centimorgans or less from a disease-resistance gene allele, wherein the marker comprises the polynucleotide sequence of SEQ ID NO: 2 (SSLP090), or a polynucleotide sequence that is completely complementary to SEQ ID NO: 2, and wherein the disease-resistance gene allele is the resistant allele of the soybean mosaic virus resistance gene 4 (Rsv4); and,
   b) selecting a plant comprising the marker nucleic acid, thereby selecting a disease-resistant plant.

8. The method of claim 7, wherein the detecting comprises amplifying the marker nucleic acid or a portion of the marker nucleic acid and detecting the resulting amplified marker nucleic acid and wherein the amplifying produces a marker amplicon.

9. The method of claim 8, wherein the amplifying comprises performing a polymerase chain reaction (PCR) using one or more nucleic acid from the plant as a template in the PCR.

10. The method of claim 9, wherein the PCR comprises a primer pair having the nucleotide sequence of SEQ ID NOs: 5 and 6.

11. The method of claim 7, wherein the soybean plant is a progeny plant resulting from a plant cross between a first plant comprising the disease-resistance gene allele and a second plant that does not comprise the disease-resistance gene allele.

12. The method of claim 11, wherein the method further comprises introgressing the disease-resistance gene allele into offspring of the progeny soybean plant.

13. The method of claim 1, wherein the polynucleotide sequence is SEQ ID NO: 1 (SSLP039).

14. The method of claim 7, wherein the polynucleotide sequence is SEQ ID NO: 2 (SSLP090).

* * * * *

SEQUENCE LISTING

<160> NUMBER OF SEQ ID NOS: 9

<210> SEQ ID NO 1
<211> LENGTH: 532
<212> TYPE: DNA
<213> ORGANISM: Glycine max

<400> SEQUENCE: 1
gcacgagaga gaatacacca aaacccaaca tgaaaaccct taacaaagcc tcacttattt      60
tattccctct cttgttcctt tccctattca agcattccca tgctgcagga atcgctgtct     120
actggggcca aaacggtgga gaaggcacct tagcagaagc ttgcaacact agaaactacc     180
aatatgtgaa catagccttc ttgtccactt tggcaacgg ccaaactcca caactcaacc      240
ttgcaggtca ttgtgacccc aacaacaatg gctgcactgg gttgagcagt gacatcaaaa     300
cttgccaaga ccttggcatc aaagtgttgc tctcccttgg tggtggtgct ggaagctact     360

```
ccctcagctc agctgatgat gccactcaac ttgcaaacta cctctggcag aatttccttg      420
gaggtcaaac cggatcaggg ccattaggta atgttatatt ggatggcatt gactttgaca      480
ttgaatctgg tgggagtgac cattatgatg acctagccag ggcattaaat ag             532

<210> SEQ ID NO 2
<211> LENGTH: 412
<212> TYPE: DNA
<213> ORGANISM: Glycine max

<400> SEQUENCE: 2
gaaatttcca aggactagtt cccttactca tcttttggaa atggattact tgggtccaat       60
atcacatata ttatctgatg ccacatacaa ttcaaccttt gattttcaaa ttaacactgc      120
caatggtgga atagacccgt tcgtaaaacc acagccggtt gaaatcccct tatgcagcaga     180 ttcagggaag taccaagtga acaaaatag caccatcaac cccaccatat tgtgaaccca      240
agtgtattat caaagaggat aatgccaaaa aaatattaa aaaaaatgaa attggattat       300
ttggacatga cgataagcgt caccaattaa ataatcctga agttctttgt aaatatatat      360
atatatatat atatatatat atatatatat atatatatat atatatatat at             412

<210> SEQ ID NO 3
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 3
gcctcactta ttttattccc tctc                                              24

<210> SEQ ID NO 4
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 4
gcccagtgca gccattgttg t                                                 21

<210> SEQ ID NO 5
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 5
ttggattatt tggacatgac gata                                              24

<210> SEQ ID NO 6
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 6
ggggagtgtt acttaatgaa tggta                                             25

<210> SEQ ID NO 7
```

<211> LENGTH: 176
<212> TYPE: PRT
<213> ORGANISM: Glycine max

<400> SEQUENCE: 7

Thr Arg Glu Asn Thr Pro Lys Pro Asn Met Lys Thr Leu Asn Lys Ala
1               5                   10                  15

Ser Leu Ile Leu Phe Pro Leu Leu Phe Leu Ser Leu Phe Lys His Ser
            20                  25                  30

His Ala Ala Gly Ile Ala Val Tyr Trp Gly Gln Asn Gly Gly Glu Gly
        35                  40                  45

Thr Leu Ala Glu Ala Cys Asn Thr Arg Asn Tyr Gln Tyr Val Asn Ile
    50                  55                  60

Ala Phe Leu Ser Thr Phe Gly Asn Gly Gln Thr Pro Gln Leu Asn Leu
65                  70                  75                  80

Ala Gly His Cys Asp Pro Asn Asn Gly Cys Thr Gly Leu Ser Ser
                85                  90                  95

Asp Ile Lys Thr Cys Gln Asp Leu Gly Ile Lys Val Leu Leu Ser Leu
            100                 105                 110

Gly Gly Gly Ala Gly Ser Tyr Ser Leu Ser Ser Ala Asp Asp Ala Thr
        115                 120                 125

Gln Leu Ala Asn Tyr Leu Trp Gln Asn Phe Leu Gly Gly Gln Thr Gly
    130                 135                 140

Ser Gly Pro Leu Gly Asn Val Ile Leu Asp Gly Ile Asp Phe Asp Ile
145                 150                 155                 160

Glu Ser Gly Gly Ser Asp His Tyr Asp Asp Leu Ala Arg Ala Leu Asn
                165                 170                 175

<210> SEQ ID NO 8
<211> LENGTH: 167
<212> TYPE: PRT
<213> ORGANISM: Glycine max

<400> SEQUENCE: 8

Met Lys Thr Leu Asn Lys Ala Ser Leu Ile Leu Phe Pro Leu Leu Phe
1               5                   10                  15

Leu Ser Leu Phe Lys His Ser His Ala Ala Gly Ile Ala Val Tyr Trp
            20                  25                  30

Gly Gln Asn Gly Gly Glu Gly Thr Leu Ala Glu Ala Cys Asn Thr Arg
        35                  40                  45

Asn Tyr Gln Tyr Val Asn Ile Ala Phe Leu Ser Thr Phe Gly Asn Gly
    50                  55                  60

Gln Thr Pro Gln Leu Asn Leu Ala Gly His Cys Asp Pro Asn Asn
65                  70                  75                  80

Gly Cys Thr Gly Leu Ser Ser Asp Ile Lys Thr Cys Gln Asp Leu Gly
                85                  90                  95

Ile Lys Val Leu Leu Ser Leu Gly Gly Gly Ala Gly Ser Tyr Ser Leu
            100                 105                 110

Ser Ser Ala Asp Asp Ala Thr Gln Leu Ala Asn Tyr Leu Trp Gln Asn
        115                 120                 125

Phe Leu Gly Gly Gln Thr Gly Ser Gly Pro Leu Gly Asn Val Ile Leu
    130                 135                 140

Asp Gly Ile Asp Phe Asp Ile Glu Ser Gly Gly Ser Asp His Tyr Asp
145                 150                 155                 160

Asp Leu Ala Arg Ala Leu Asn
                165

```
<210> SEQ ID NO 9
<211> LENGTH: 86
<212> TYPE: PRT
<213> ORGANISM: Glycine max

<400> SEQUENCE: 9

Lys Phe Pro Arg Thr Ser Ser Leu Thr His Leu Leu Glu Met Asp Tyr
1               5                   10                  15

Leu Gly Pro Ile Ser His Ile Leu Ser Asp Ala Thr Tyr Asn Ser Thr
                20                  25                  30

Phe Asp Phe Gln Ile Asn Thr Ala Asn Gly Gly Ile Asp Pro Phe Val
            35                  40                  45

Lys Pro Gln Pro Val Glu Ile Pro Tyr Ala Ala Asp Ser Gly Lys Tyr
        50                  55                  60

Gln Val Lys Gln Asn Ser Thr Ile Asn Pro Thr Ile Phe Val Asn Gln
65                  70                  75                  80

Val Tyr Tyr Gln Arg Gly
                85
```